United States Patent
Rosselli et al.

(10) Patent No.: US 10,464,935 B2
(45) Date of Patent: Nov. 5, 2019

(54) SPECIFIC N AND P ACTIVE MATERIALS FOR ORGANIC PHOTOELECTRIC CONVERSION LAYERS IN ORGANIC PHOTODIODES

(71) Applicant: Sony CORPORATION, Tokyo (JP)

(72) Inventors: Silvia Rosselli, Stuttgart (DE); Nikolaus Knorr, Stuttgart (DE); Tzenka Miteva, Stuttgart (DE); Gabriele Nelles, Stuttgart (DE); Vitor Deichmann, Stuttgart (DE); David Danner, Stuttgart (DE); William E. Ford, Stuttgart (DE); Dennis Chercka, Stuttgart (DE); Vladimir Yakutkin, Stuttgart (DE); Lars-Peter Scheller, Stuttgart (DE)

(73) Assignee: Sony CORPORATION, Tokyo (JP)

(*) Notice: Subject to any disclaimer, the term of this patent is extended or adjusted under 35 U.S.C. 154(b) by 0 days.

(21) Appl. No.: 15/558,578

(22) PCT Filed: Mar. 31, 2016

(86) PCT No.: PCT/EP2016/057165
§ 371 (c)(1),
(2) Date: Sep. 15, 2017

(87) PCT Pub. No.: WO2016/156546
PCT Pub. Date: Oct. 6, 2016

(65) Prior Publication Data
US 2018/0057492 A1  Mar. 1, 2018

(30) Foreign Application Priority Data
Mar. 31, 2015 (EP) .................................... 15162042

(51) Int. Cl.
*C07D 471/06* (2006.01)
*H01L 51/00* (2006.01)
(Continued)

(52) U.S. Cl.
CPC .......... *C07D 471/06* (2013.01); *H01L 27/286* (2013.01); *H01L 27/307* (2013.01);
(Continued)

(58) Field of Classification Search
None
See application file for complete search history.

(56) References Cited

U.S. PATENT DOCUMENTS

| 6,387,727 B1 | 5/2002 | Katz et al. |
| 7,569,693 B2 | 8/2009 | Marks et al. |

(Continued)

FOREIGN PATENT DOCUMENTS

| CN | 103889985 A | 6/2014 |
| EP | 1 340 755 A1 | 9/2003 |

(Continued)

OTHER PUBLICATIONS

Eilaf Ahmed, et al., "Design of New Electron Acceptor Materials for Organic Photovoltaics: Synthesis, Electron Transport, Photophysics, and Photovoltaic Properties of Oligothiophene-Functionalized Naphthalene Diimides" Chemistry of Materials, 2011, 23, pp. 4563-4577.*

(Continued)

*Primary Examiner* — Erik Kielin
(74) *Attorney, Agent, or Firm* — Oblon, McClelland, Maier & Neustadt, L.L.P.

(57) ABSTRACT

The field of the DISCLOSURE lies in active materials for organic image sensors. The present disclosure relates to naphthalene diimide-based molecules and naphthalene diimide dimer-based molecules. The present disclosure relates to (Continued)

transparent N materials and/or to transparent P materials including the molecule(s) according to the present disclosure and their use in absorption layer(s), photoelectric conversion layer(s) and/or an organic image sensor and methods for their synthesis. The present disclosure also relates to photoelectric conversion layer(s) including an active material according to the present disclosure, to a device, including active material(s) according to the present disclosure or photoelectric conversion layer(s) according to the present disclosure. Moreover, the present disclosure relates to an organic image sensor including photoelectric conversion layer(s) according to the present disclosure.

14 Claims, 28 Drawing Sheets

(51) Int. Cl.
  H01L 51/42      (2006.01)
  H01L 27/28      (2006.01)
  H01L 27/30      (2006.01)
(52) U.S. Cl.
  CPC ...... *H01L 51/0053* (2013.01); *H01L 51/0062* (2013.01); *H01L 51/0067* (2013.01); *H01L 51/0072* (2013.01); *H01L 51/4253* (2013.01); *Y02E 10/549* (2013.01); *Y02P 70/521* (2015.11)

(56) References Cited

U.S. PATENT DOCUMENTS

| | | | |
|---|---|---|---|
| 8,309,394 B2 | 11/2012 | Shukla et al. | |
| 2004/0116493 A1 | 6/2004 | Sugimori et al. | |
| 2007/0160905 A1 | 7/2007 | Morishita et al. | |
| 2008/0300405 A1* | 12/2008 | Konemann | C07D 471/06 544/245 |
| 2012/0211082 A1 | 8/2012 | Akiyama et al. | |
| 2013/0235176 A1* | 9/2013 | Miyano | G02B 13/06 348/65 |
| 2014/0021448 A1* | 1/2014 | Polander | H01L 51/0072 257/40 |
| 2014/0213789 A1 | 7/2014 | Polander et al. | |
| 2015/0051398 A1 | 2/2015 | Schimperna et al. | |
| 2016/0064457 A1* | 3/2016 | Lee | H01L 27/307 257/40 |

FOREIGN PATENT DOCUMENTS

| | | | |
|---|---|---|---|
| JP | 2010-141268 A | 6/2010 | |
| KR | 10-2014-0040716 A | 4/2014 | |
| KR | 10-2014-0144845 A | 12/2014 | |
| WO | 2006/100545 A1 | 9/2006 | |
| WO | 2012/142460 A1 | 10/2012 | |
| WO | 2013/024409 A1 | 2/2013 | |
| WO | WO-2013096915 A1 * | 6/2013 | ........... C07D 471/06 |
| WO | 2013/140328 A1 | 9/2013 | |
| WO | 2014/200249 A1 | 12/2014 | |

OTHER PUBLICATIONS

Brooks A. Jones, et al., Cyanonaphthalene diimide semiconductors for air-stable, flexible, and optically transparent n-channel field-effect transistors, Chemistry of Materials, vol. 19, No. 11, 2007, (2 pages), (Abstract only).

Deepak Schukla, et al., "Thin-Film Morphology Control in Naphthalene-Diimide-Based Semiconductors: High Mobility n-Type Semiconductor for Organic Thin-Film Transistors," Chemistry of Materials, vol. 20, No. 24, Dec. 2, 2008, (3 pages), (Abstract only).

M. Stolte, et al., "Organic n-channel thin film transistors based on dichlorinated naphthalene diimides," SPIE Proceedings, vol. 7778, Materials I, Aug. 17, 2010, (3 pages), (Abstract only).

Hua Ke, et al., "Electron-deficient naphthalene diimides as efficient planar π-acid organocatalysts for selective oxidative C-C coupling of 2,6-di-*tert*-butylphenol: A temperature effect," Journal of Molecular Catalysis A: Chemical, vol. 385, 2014, pp. 26-30.

Kevin C. See, et al., "Easily Synthesized Naphthalene Tetracarboxylic Diimide Semiconductors with High Electron Mobility in Air," Chem. Mater., vol. 20, No. 11, 2008, pp. 3609-3616.

Song Guo, et al., "Room-Temperature Long-Lived Triplet Excited States of Naphthalenediimides and Their Applications as Organic Triplet Photosensitizers for Photooxidation and Triplet-Triplet Annihilation Upconversions," The Journal of Organic Chemistry, vol. 77, 2012, pp. 3933-3943.

Gayane Koshkakaryan, et al., "Alternative Donor-Acceptor Stacks from Crown Ethers and Naphthalene Diimide Derivatives: Rapid, Selective Formation from Solution and Solid State Grinding," J. Am. Chem. Soc. 2009, vol. 131, 2009, pp. 2078-2079.

Guo-Bi Li, et al., "Construction of OD to 3D cadmium complexes from different pyridyl diimide ligands," Dalton Trans., vol. 41, 2012, pp. 4626-4633.

Diego Villamaina, et al., "Excited-state dynamics of porphyrin-naphthalenediimide-porphyrin triads," Phys. Chem. Chem. Phys., vol. 15, 2013, pp. 1177-1187.

Sheshanath V. Bhosale, et al., "The synthesis of novel core-substituted naphthalene diimides via Suzuki cross-coupling and their properties," New Journal of Chemistry, vol. 33, 2009, pp. 2409-2413.

W. J. Sep, et al., "Pronounced Solvatochromism of Charge-Transfer Complexes in Strongly Hydrogen Bonding Solvents," Laboratory for Organic Chemistry, Oct. 25, 1974, (6 pages).

Adriano Defini Andricopulo, et al., "Analgesic activity of cyclic imides: 1,8-naphthalimide and 1,4,5,8-naphthalenediimide derivatives," Il Farmaco, XP002907644, vol. 55, 2000, pp. 319-321.

Howard E. Katz, et al., "Naphthalenetetracarboxylic Diimide-Based n-Channel Transistor Semiconductors: Structural Variation and Thiol-Enhanced Gold Contacts," J. Am. Chem. Soc. 2000, XP007909204, vol. 122, Jul. 26, 2000, pp. 7787-7792.

Frederique Chaignon, et al., "Very large acceleration of the photoinduced electron transfer in a Ru(bpy)$_3$-naphthalene bisimide dyad bridged on the naphthyl core," Chem. Commun., 2007, pp. 64-66.

Filippo Doria, et al., "Substituted Heterocyclic Naphthalene Diimides with Unexpected Acidity, Synthesis, Properties, and Reactivity," J. Org. Chem. 2009, Oct. 22, 2009, vol. 74, pp. 8616-8625.

Stephanie Chopin, et al., "Syntheses and properties of core-substituted naphthalene bisimides with aryl ethynyl or cyano groups," Journal of Materials Chemistry, vol. 17, 2007, pp. 4139-4146.

International Search Report and Written Opinion dated May 30, 2016 in PCT/EP2016/057165 filed Mar. 31, 2016.

Office Action dated Oct. 29, 2018 in Korean Patent Application No. 10-2017-7027506 (with English language translation).

Notice of Preliminary Report dated Apr. 12, 2018 in Korean Patent Application No. 10-2017-7027506 (with English language translation).

Search Report and Office Action dated Jul. 4, 2019 issued in corresponding Chinese patent application No. 201680020043.3 (with English translation).

\* cited by examiner without MoO3 with MoO3

Figure 16

| Material | DMF solution | | TF-film |
|---|---|---|---|
| | Abs. max., nm | Ems. max., nm | Abs. max., nm |
| NDI21 | 382 | 423 | 381 |
| NDI23 | 383 | 405, 429 | 378 |
| NDI24 | 379 | 401, 425 | 385 |
| NDI26 | 379 | 431, 540 | 403 |
| NDI28 | 379 | 402, 430, 570 | 381 |
| NDI29 | 385 | 429, 554 | 375 |
| NDI35 | 380 | 432, 570 | 394 |
| NDI36 | 382 | 425, 530 | 387 |
| NDI37 | 382 | 504 | 387 |
| NDI38 | 380 | 430, 530 | 385 |

Figure 19 A

| Material | Structure | HOMO calc (TM) | LUMO calc (TM) | HOMO exp (Au/ITO) | LUMO exp (Au/ITO) | Ef Exp (Au/ITO) | Sublimation | Decomposition |
|---|---|---|---|---|---|---|---|---|
| NDI21 | 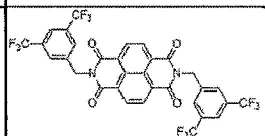 | -7.614 | -4.007 | -8.6 / -9.0 | -5.5 / -5.9 | -5.1 / -5.3 | 170°C | 270°C |
| NDI23 | 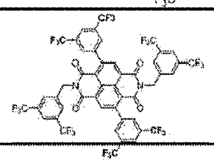 | -7.817 | -4.343 | -8.1 / -8.4 | -5.1 / -5.3 | -4.9 / -5.2 | 210°C | - |
| NDI24 | 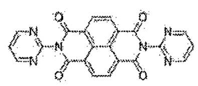 | -7.128 | -3.492 | -7.1 / -7.3 | -4.0 / -4.3 | -4.0 / -4.3 | - | 380°C |
| NDI26 | 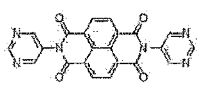 | -7.301 | -3.999 | -7.8 / -8.5 | -4.9 / -5.6 | -4.4 / -5.2 | 250°C | 400°C |
| NDI28 | 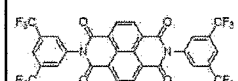 | -7.685 | -4.059 | -8.2 / -8.7 | -5.1 / -5.6 | -4.7 / -5.1 | 180°C | 300°C |

Figure 19 B

| Material | Structure | HOMO calc (TM) | LUMO calc (TM) | HOMO exp (Au/ITO) | LUMO exp (Au/ITO) | Ef Exp (Au/ITO) | Sublimation | Decomposition |
|---|---|---|---|---|---|---|---|---|
| NDI29 | 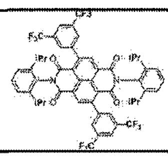 | -6.809 | -3.953 | -7.5 / -7.7 | -4.4 / -4.6 | -4.4 / -4.7 | 180°C | 340°C |
| NDI35 | 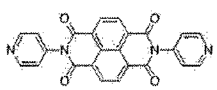 | -7.379 | -3.833 | -7.6 / -7.9 | -4.6 / -5.0 | -4.0 / -4.3 | 200°C | 360°C |
| NDI36 | 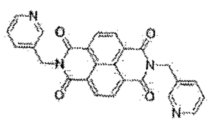 | -7.065 | -3.756 | -7.4 / -7.6 | -4.3 / -4.6 | -3.8 / -4.1 | 180°C | 340°C |
| NDI37 | 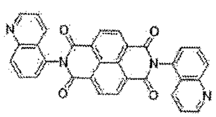 | -6.766 | -3.731 | -6.9 / -7.2 | -3.9 / -4.2 | -3.9 / -4.2 | 300°C | 380°C |
| NDI38 | 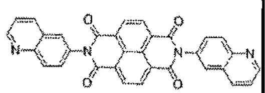 | -6.742 | -3.658 | -6.9 / -7.1 | -3.9 / -4.1 | -3.9 / -4.2 | 300°C | 420°C |

| | |
|---|---|
| LiF | 150 nm |
| AlSiCu | 100 nm |
| NDI35 | 10 nm |
| DTT9:F6-OC6F5 (1:1) | 200 nm |
| ST1163 | 10 nm |
| ITO | |
| glass | |

DTT2

DTT9

| Material | i-layer | p-buffer | n-buffer | ANL | EQE 0V | EQE -1V | $J_{dark}$ A/cm² | EDE, % | Mobility i-layer cm²/Vs |
|---|---|---|---|---|---|---|---|---|---|
| DTT2 | DTT2:F6-OC6F5 (1:1) 200nm | ST1163 10nm | NDI35 10nm | as depo | 17.5 | 21.6 | 2.9E-10 | NM | 1E-9 to 1E-7 |
| DTT9 | DTT9:F6-OC6F5 (1:1) 200nm | ST1163 10nm | NDI35 10nm | as depo | 5.4 | 7.4 | 2.5E-9 | 17 ± 3 | 1E-10 |
| DTT10 | DTT10:F6-OC6F5 (1:1) 200nm | HTM065 10nm | NDI35 10nm | as depo | 4.4 | 6.9 | 2.4E-10 | 65 ± 3 | |
| DTT11 | DTT11:F6-OC6F5 (1:1) 210nm | HTM065 10nm | NDI35 10nm | as depo | 9.4 | 11.8 | 2.8E-10 | 15 ± 3 | |

| | HOMO eV | LUMO eV |
|---|---|---|
| | -5.6 | -2.3 |
| | | |
| | | |
| | | |

| | |
|---|---|
| LiF | 150 nm |
| AlSiCu | 100 nm |
| NDI35 | 10 nm |
| DTT9:F6-OC6F5 (1:1) | 200 nm |
| HTM065 | 10 nm |
| ITO | |
| glass | |

| Material | i-layer | p-buffer | n-buffer | ANL | EQE 0V | EQE -1V | J$_{dark}$ A/cm$^2$ | EDE, % | Mobility i-layer cm$^2$/Vs | HOMO eV | LUMO eV |
|---|---|---|---|---|---|---|---|---|---|---|---|
| DTT2 | DTT2:F6-OC6F5 (1:1) 200nm | ST1163 10nm | NDI35 10nm | as depo | 17.5 | 21.6 | 2.9E-10 | NM | 1E-9 to 1E-7 | -5.6 | -2.3 |
| DTT9 | DTT9:F6-OC6F5 (1:1) 200nm | ST1163 10nm | NDI35 10nm | as depo | 5.4 | 7.4 | 2.5E-9 | 17 ± 3 | 1E-10 | | |
| DTT10 | DTT10:F6-OC6F5 (1:1) 200nm | HTM065 10nm | NDI35 10nm | as depo | 4.4 | 6.9 | 2.4E-10 | 65 ± 3 | | | |
| DTT11 | DTT11:F6-OC6F5 (1:1) 210nm | HTM065 10nm | NDI35 10nm | as depo | 9.4 | 11.8 | 2.8E-10 | 15 ± 3 | | | |

SPECIFIC N AND P ACTIVE MATERIALS FOR ORGANIC PHOTOELECTRIC CONVERSION LAYERS IN ORGANIC PHOTODIODES

BACKGROUND

The field of the DISCLOSURE lies in active materials for organic image sensors.

The present disclosure relates to naphthalene diimide-based molecules and naphthalene diimide dimer-based molecules.

The present disclosure relates to transparent N materials and/or to transparent P materials including the molecule(s) according to the present disclosure and their use in absorption layers), photoelectric conversion layers) and/or an organic image sensor and methods for their synthesis.

The present disclosure also relates to photoelectric conversion layer(s) including an active material according to the present disclosure, to a device, including active material(s) according to the present disclosure or photoelectric conversion layer(s) according to the present disclosure.

Moreover, the present disclosure relates to an organic image sensor including photoelectric conversion layer(s) according to the present disclosure.

DESCRIPTION OF THE RELATED ART

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

Image sensors, which are semiconductor devices for converting an optical image into an electric signal, include a light-sensing unit for sensing light and a logic circuit unit for processing the sensed light into an electrical signal to store data.

In the state of the art, the light-sensing unit includes a color filter and a photoelectric conversion film, a semiconductor p-n junction, such as silicon. The color filter separates light according to colors, but reduces the spatial resolution and light collection and utilization efficiency.

In order to overcome this problem geometries are reported where photoelectric conversion units capable of detecting light of different wavelengths are stacked in a longitudinal direction. In particular such photoelectrical conversion unit is an organic photoelectric conversion layer based on p-n junction or bulk heterojunction. The photoelectric conversion efficiency of such a unit depends strongly on the type of materials used in the layer. With the organic materials available so far, low conversion efficiencies and high dark currents are reported.

In another solution, an organic layer is used that is capable to absorb in the IR region but not in the visible region, that could be combined with a complementary metal oxide semiconductor (CMOS) based imager pan for the visible range or with an organic based imager part that could absorb in the visible range. In both cases white light is collected and filter have to be used to get the BGR pixel resolution. In this case, as well as in the case of color filter, light is separated according to colors but the spatial resolution and light collection and utilization efficiency is reduced.

SUMMARY

The present disclosure provides a naphthalene diimide (NDI)-based molecule represented by the general formula I

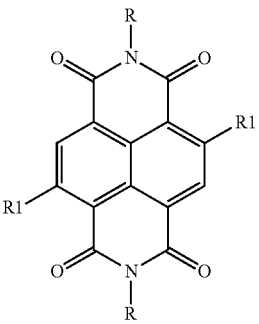

wherein
R is, at each occurrence, independently selected from
—$C_xH_{2x+1}$, —$C_xX_{2x+1}$, —$C_xH_2X_{2x-1}$,

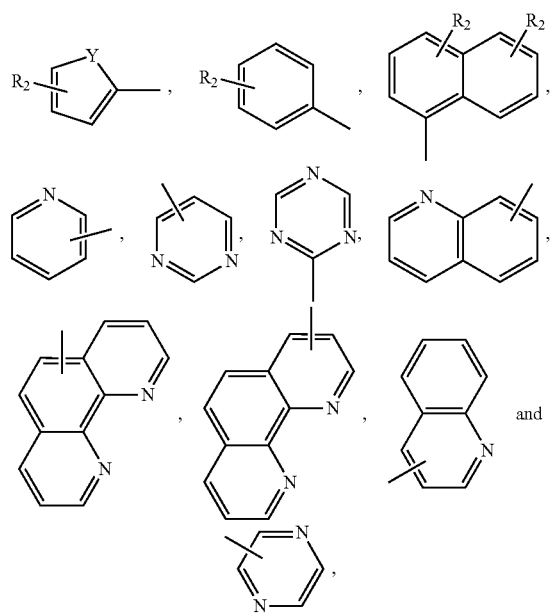

and
$R_1$ is, at each occurrence, independently selected from

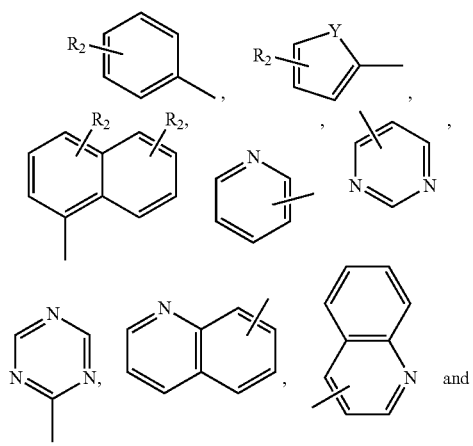

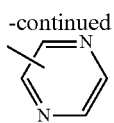

x is an integer from 1 to 10,
X is halogen (F, Cl, Br, I),
Y is selected from CH$_2$, S, O, Se and N—R$_2$,
R$_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group.

The present disclosure provides a naphthalene diimide (NDI)-based molecule represented by the general formula Ia

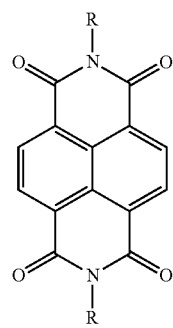

Ia wherein
R is, at each occurrence, independently selected from —C$_x$H$_{2x+1}$, —C$_x$X$_{2x+1}$, —C$_x$H$_2$X$_{2x-1}$,

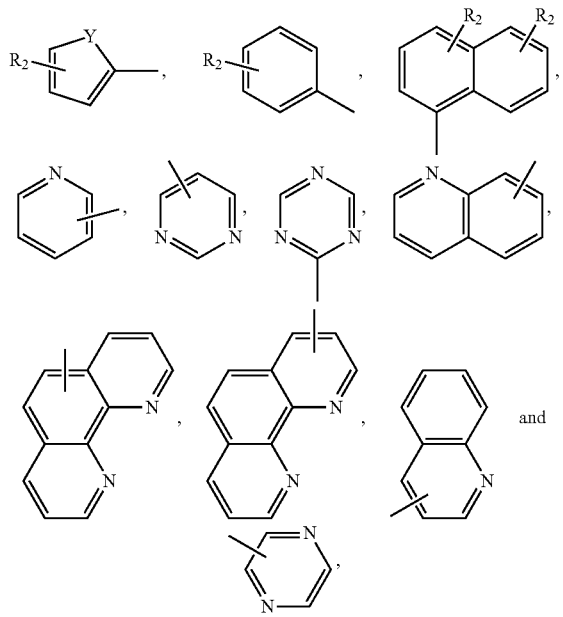

and
x is an integer from 1 to 10,
X is halogen (F, Cl, Br, I),
Y is selected from CH$_2$, S, O, Se and N—R$_2$,
R$_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group.

The present disclosure provides a naphthalene diimide (NDI-NDI)-based molecule represented by the general formula II or III

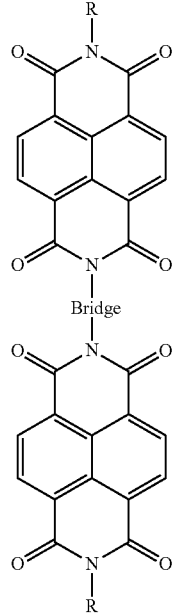

II

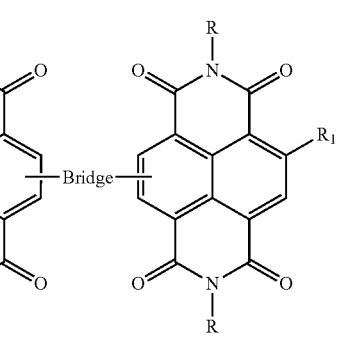

III wherein in general formula II
R is, at each occurrence, independently selected from —C$_x$H$_{2x+1}$, —C$_x$X$_{2x+1}$, —C$_x$H$_2$X$_{2x-1}$,

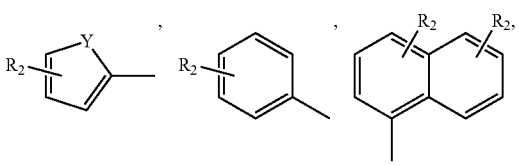

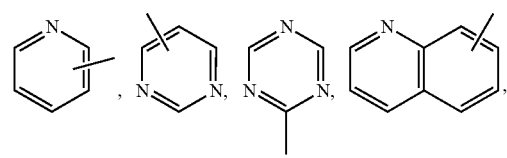

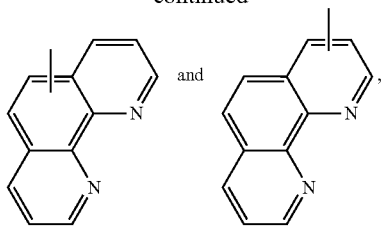 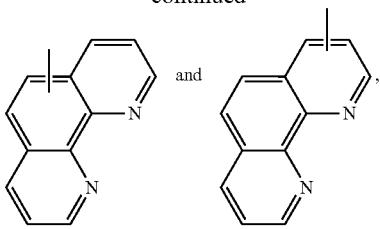

Bridge is selected

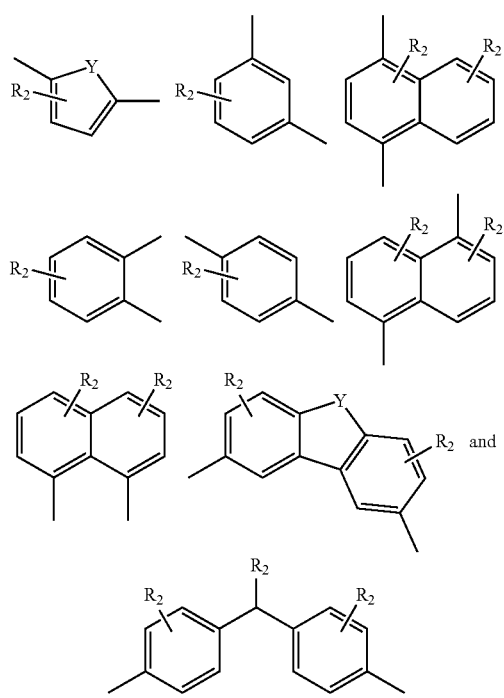

x is an integer from 1 to 10,
X is halogen (F, Cl, Br, I),
Y is selected from CH$_2$, S, O, Se and N—R$_2$,
R$_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group,
and wherein in general formula III
R is, at each occurrence, independently selected from —C$_x$H$_{2x+1}$, —C$_x$X$_{2x+1}$, —C$_x$H$_2$X$_{2x-1}$,

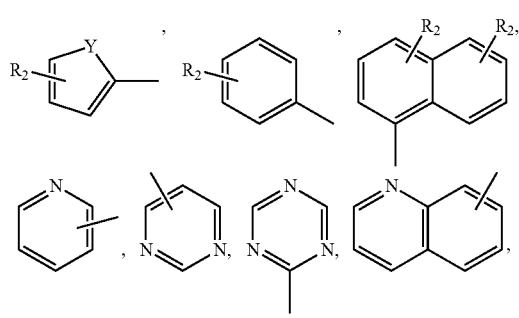

R$_1$ is, at each occurrence, independently selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated alkyl group, heteroaryl group, fluorenyl group, and
Bridge is selected x is an integer from 1 to 10,
X is halogen (F, Cl, Br, I),
Y is selected from CH$_2$, S, O, Se and N—R$_2$,
R$_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group.

The present disclosure provides a transparent N or P or ambipolar material, including a naphthalene diimide (NDI)-based molecule or a naphthalene diimide dimer (NDI-NDI)-based molecule according to the present disclosure.

The present disclosure provides a P:N heterojunction or a bi(multi) layer junction, preferably a P1:P2:N1:N2 heterojunction or multilayer junction, including
a naphthalene diimide (NDI)-based molecule or a naphthalene diimide dimer (NDI-NDI)-based molecule according to the present disclosure, or
a transparent N and/or P or ambipolar material according to the present disclosure, optionally including a further N and/or P material, wherein the further N and/or P material preferably exhibits absorption in the visible wavelength range (about 400 to about 700 nm).

The present disclosure provides the use of a naphthalene diimide (NDI)-based molecule or a naphthalene diimide dimer (NDI-NDI)-based molecule according to the present disclosure, or of a transparent N and/or P or ambipolar material according to the present disclosure in an absorption layer and/or in a photoelectric conversion layer and/or in an organic and/or hybrid module for optoelectronic application.

The present disclosure provides a photoelectric conversion layer including a naphthalene diimide (NDI)-based molecule or a naphthalene diimide dimer (NDI-NDI)-based molecule according to the present disclosure, or a transparent N and/or P or ambipolar material according to the present disclosure. The present disclosure provides an absorption layer including a naphthalene diimide (NDI)-based molecule or a naphthalene diimide dimer (NDI-NDI)-based molecule according to the present disclosure, or a transparent N and/or P or ambipolar material according to the present disclosure.

The present disclosure provides a device including naphthalene diimide (NDI)-based molecule(s) or naphthalene diimide dimer (NDI-NDI)-based molecule(s) according to the present disclosure, or transparent N and/or P or ambipolar material(s) according to the present disclosure or a photoelectric conversion layer(s) according to the present disclosure.

The present disclosure provides an organic image sensor, including an organic photoelectric conversion unit including photoelectric conversion layer(s) according to the present disclosure.

The present disclosure provides a hybrid Silicon-organic image sensor, including an organic photoelectric conversion unit including photoelectric conversion layer(s) according to the present disclosure.

The present disclosure provides a method for synthesis of transparent n materials, in particular, naphthalene diimide (NDI)-based materials, naphthalene diimide dimer (NDI dimer)-based materials, naphthalene mono-diimide dimer (NMI-NDI)-based materials.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION Of THE DRAWINGS

A more complete appreciation of the disclosure and many of the attendant advantages thereof will be readily obtained as the same becomes better understood by reference to the following detailed description when considered in connection with the accompanying drawings, wherein:

FIG. 16 shows the absorption for NDI materials with general formula Ia.
FIG. 19A and B shows energy levels of N-buffer materials with general formula Ia.

DETAILED DESCRIPTION OF THE EMBODIMENTS

Figure 1:
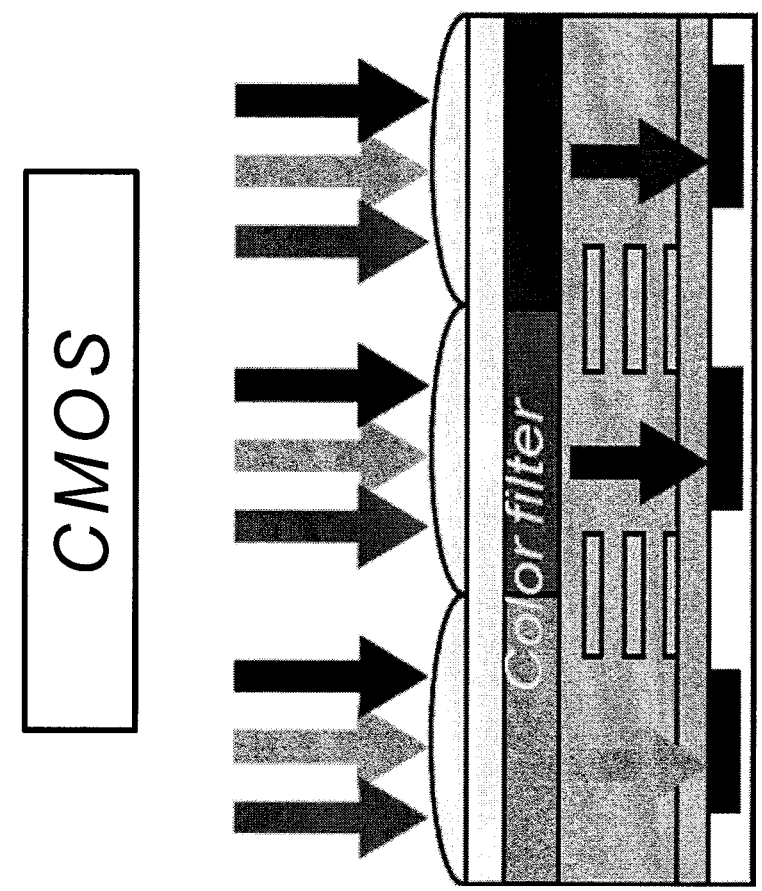
FIG. 1 shows a CMOS image sensor.

As discussed above, the present disclosure provides a naphthalene diimide (NDI)-based molecule represented by the general formula I
wherein R is, at each occurrence, independently selected from —$C_xH_{2x+1}$, —$C_xX_{2x+1}$, —$C_xH_2X_{2x-1}$, -continued

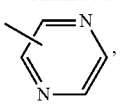

and $R_1$ is, at each occurrence, independently selected from

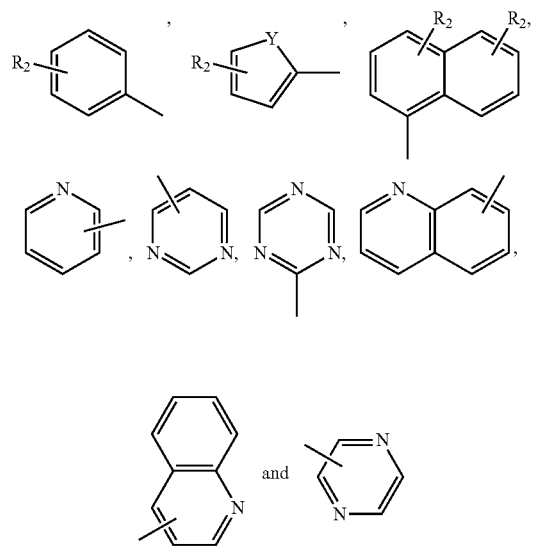

x is an integer from 1 to 10,

X is halogen (F, Cl, Br, I),

Y is selected from $CH_2$, S, O, Se and N—$R_2$, $R_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group.

In a preferred embodiment of the naphthalene diimide (NDI)-based molecule R is selected from

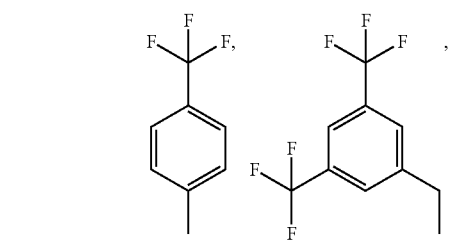

—$(CF_2)_5CF_3$, —$(CH_2)_5CH_3$, —$CH_2$—$(CF_2)_3$—$CF_3$,

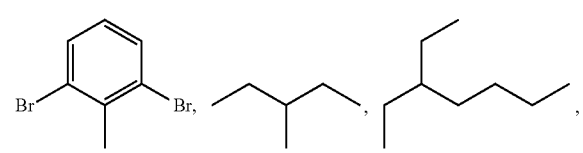

-continued

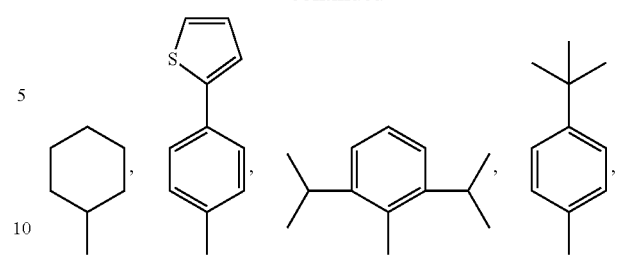

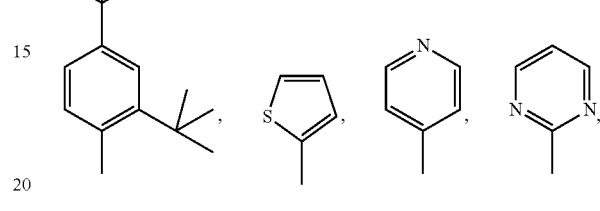

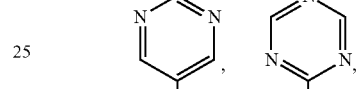

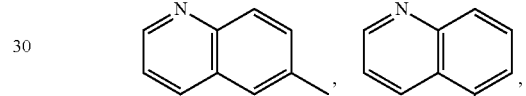

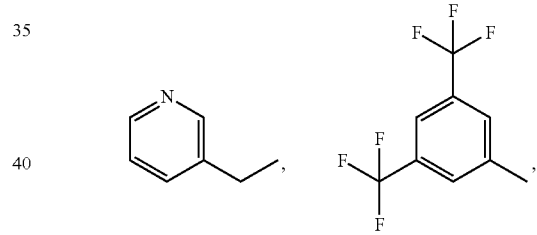

and $R_1$ is selected from

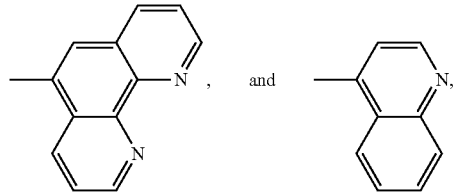

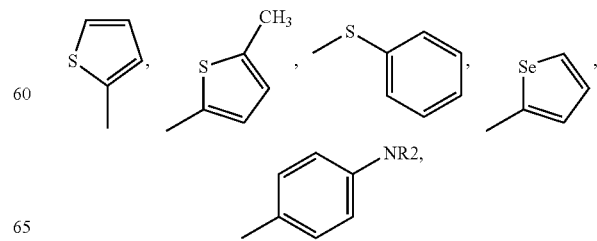

—OCH$_2$CH$_3$, —BR, —H,

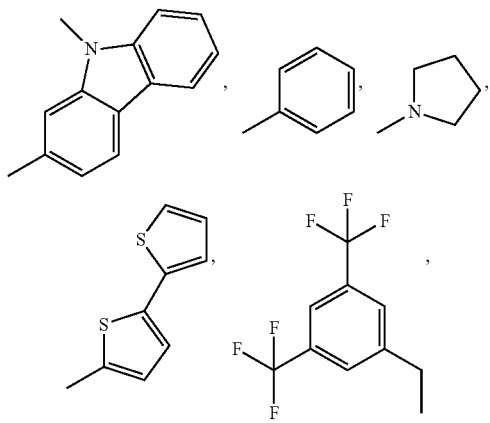

In a further preferred embodiment of the naphthalene diimide (NDI)-based molecule R is

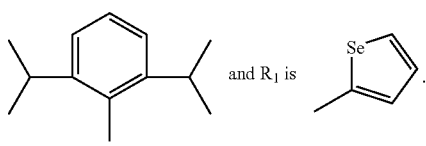

The molecule can be NDI with the following structure:

NDI 1

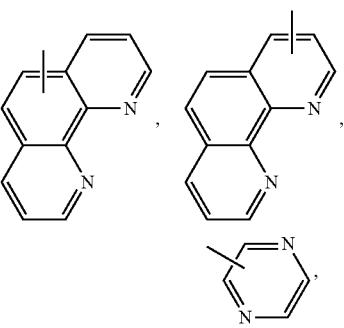

As discussed above, the present disclosure provides a naphthalene diimide (NDI)-based molecule represented by the general formula Ia Ia wherein R is, at each occurrence, independently selected from —C$_x$H$_{2x+1}$, —C$_x$X$_{2x+1}$, —C$_x$H$_2$X$_{2x-1}$, and x is an integer from 1 to 10, X is halogen (F, Cl, Br, I), Y is selected from CH$_2$, S, O, Se and N—R$_2$, R$_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group.

In a preferred embodiment of the naphthalene diimide (NDI)-based molecule
R is selected from
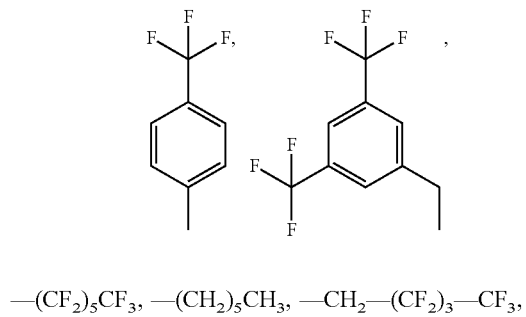
—(CF$_2$)$_5$CF$_3$, —(CH$_2$)$_5$CH$_3$, —CH$_2$—(CF$_2$)$_3$—CF$_3$,
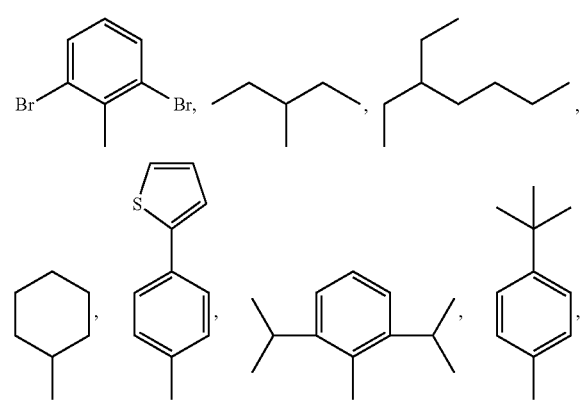
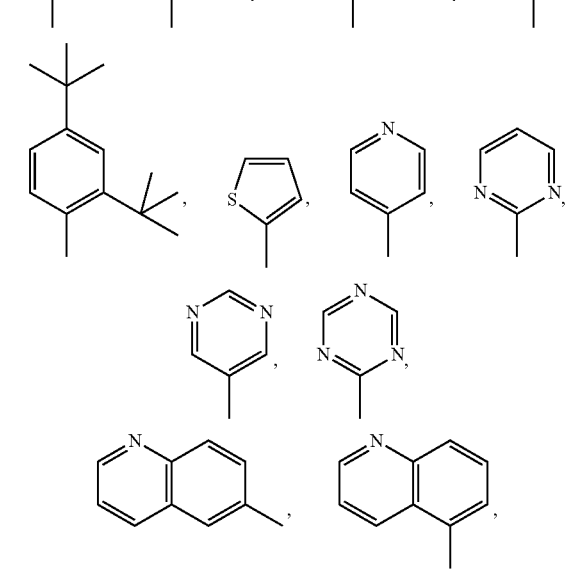
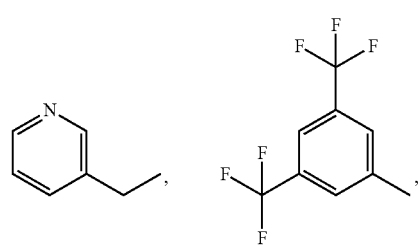
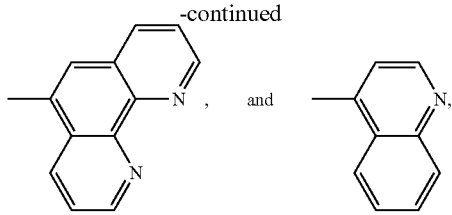
wherein in particularly R is selected
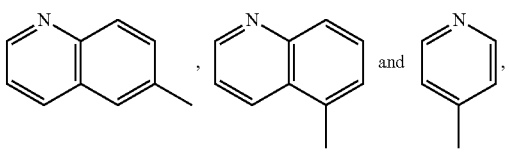
more particularly R is
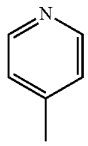
The molecule can be NDI with the following structure:
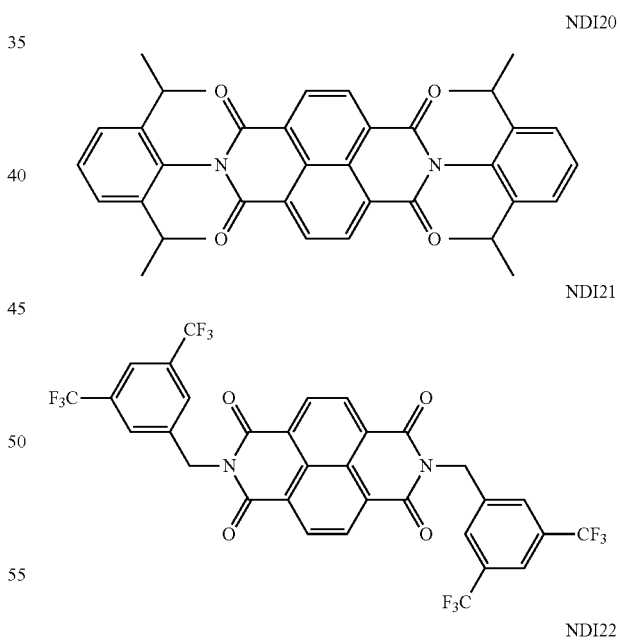
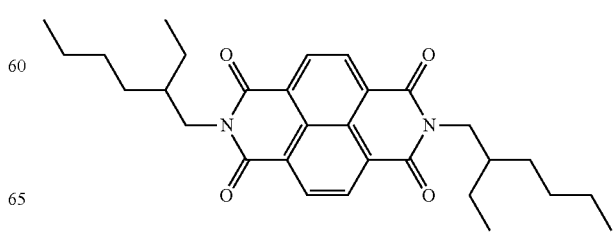

NDI23
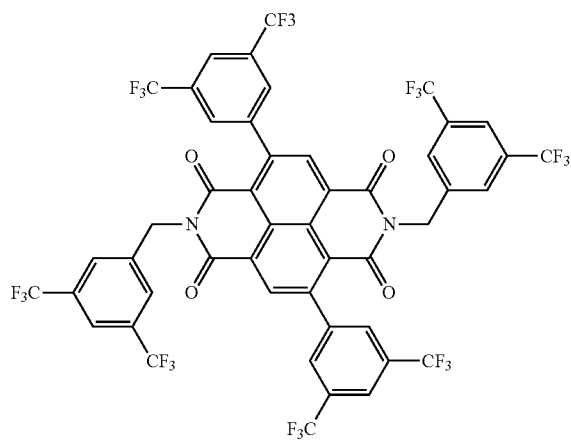
NDI24
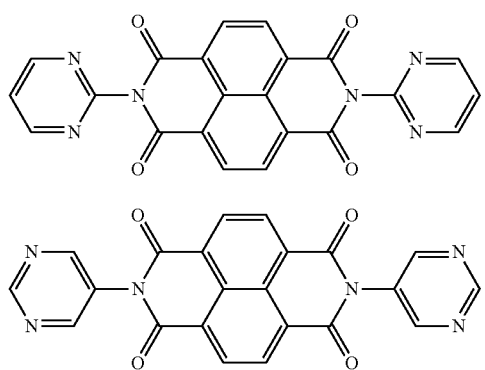
NDI26
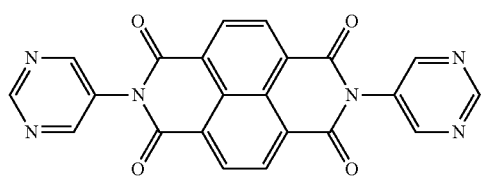
NDI28
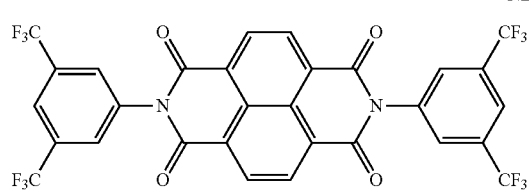
NDI29
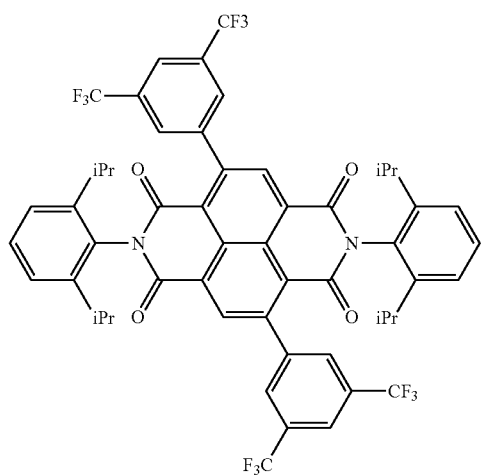
NDI35
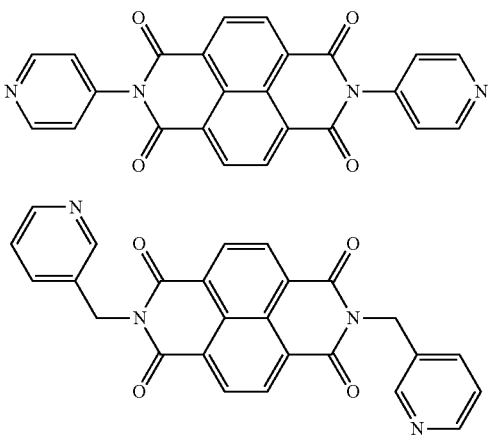
NDI36
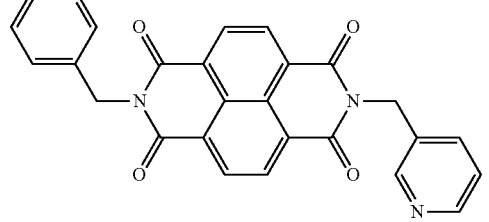
NDI37
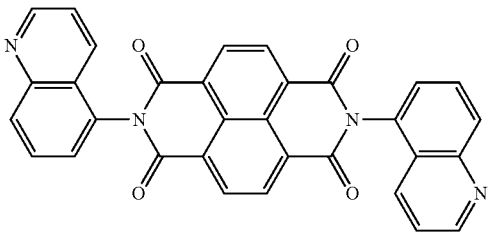
NDI38
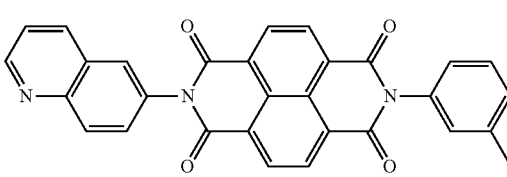
As discussed above, the present disclosure provides a naphthalene diimide dimer (NDI-NDI)-based molecule represented by the general formula II or III
II
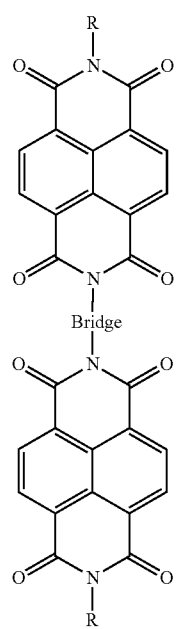

III

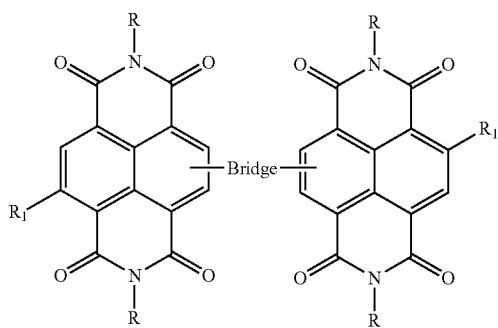

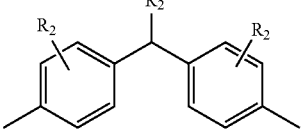

wherein general formula II
R is, at each occurrence, independently selected from —$C_xH_{2x+1}$, —$C_xX_{2x+1}$, —$C_xH_2X_{2x-1}$,

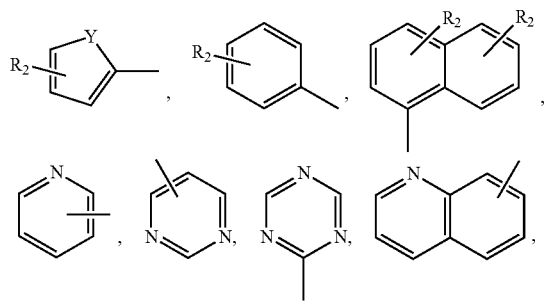

and
Bridge selected from

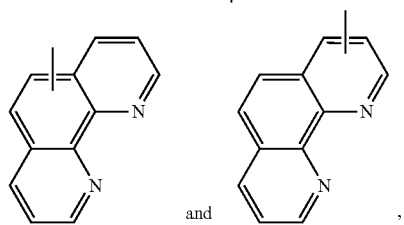

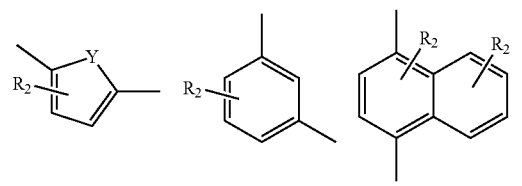

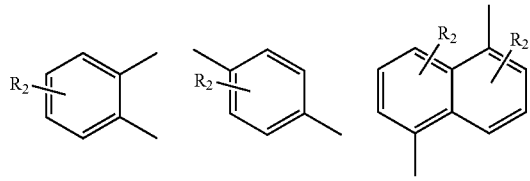

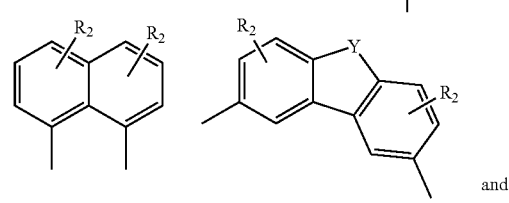

x is an integer from 1 to 10,
X is halogen (F, Cl, Br, I),
Y is selected from $CH_2$, S, O, Se and N—$R_2$,
$R_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group.
and wherein in general formula III
R is, at each occurrence, independently selected from —$C_xH_{2x+1}$, —$C_xX_{2x+1}$, —$C_xH_2X_{2x-1}$,

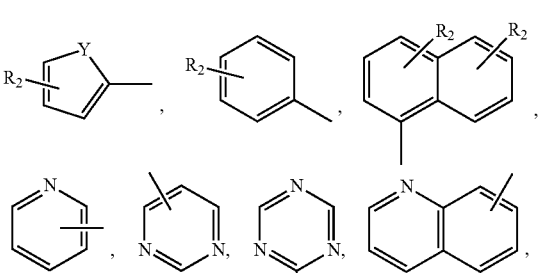

and
$R_1$ is, at each occurrence, independently selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated alkyl group, heteroaryl group, fluorenyl group, and
Bridge is selected from

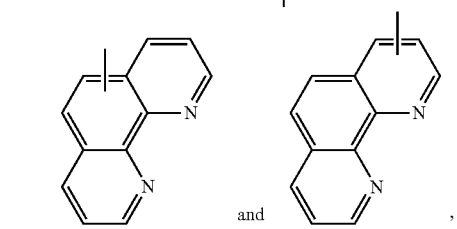

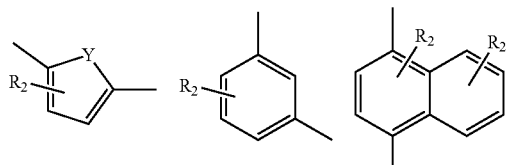

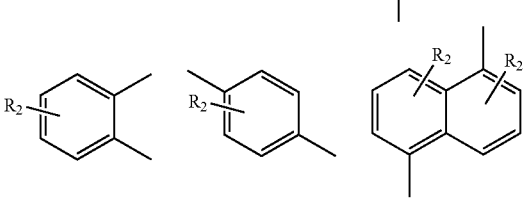

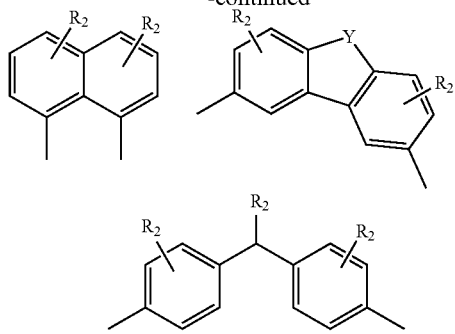
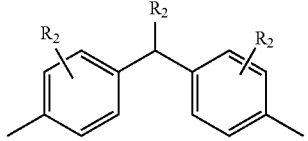

and x is an integer from 1 to 10,

X is halogen (F, Cl, Br, I),

Y is selected from CH$_2$, S, O, Se and N—R$_2$,

R$_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group.

In a preferred embodiment of the naphthalene diimide dimer (NDI-NDI)-based molecule of general formula II R is selected from

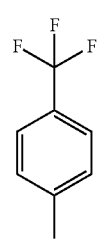
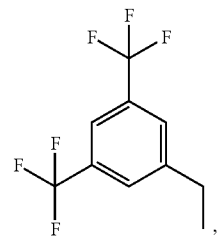

—(CF$_2$)$_5$CF$_3$, —(CH$_2$)$_5$CH$_3$, —CH$_2$—(CF$_2$)$_3$—CF$_3$,

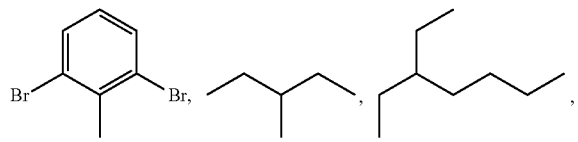

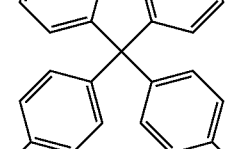
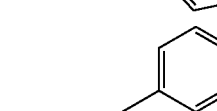
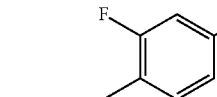

and

Bright is selected from

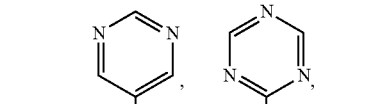
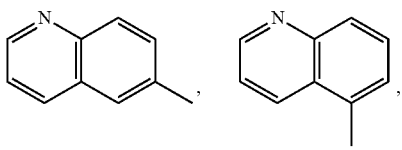
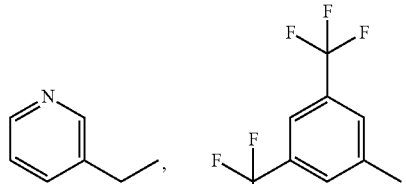
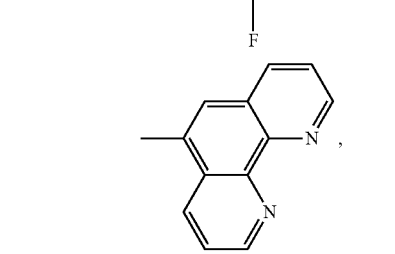

and

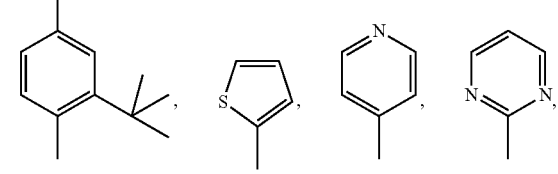
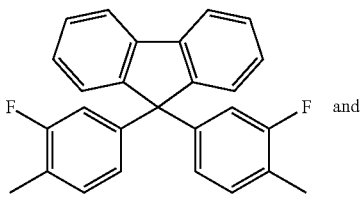

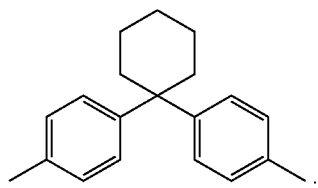
In a preferred embodiment of the naphthalene diimide dimer (NDI-NDI)-based molecule of general formula III R is selected from
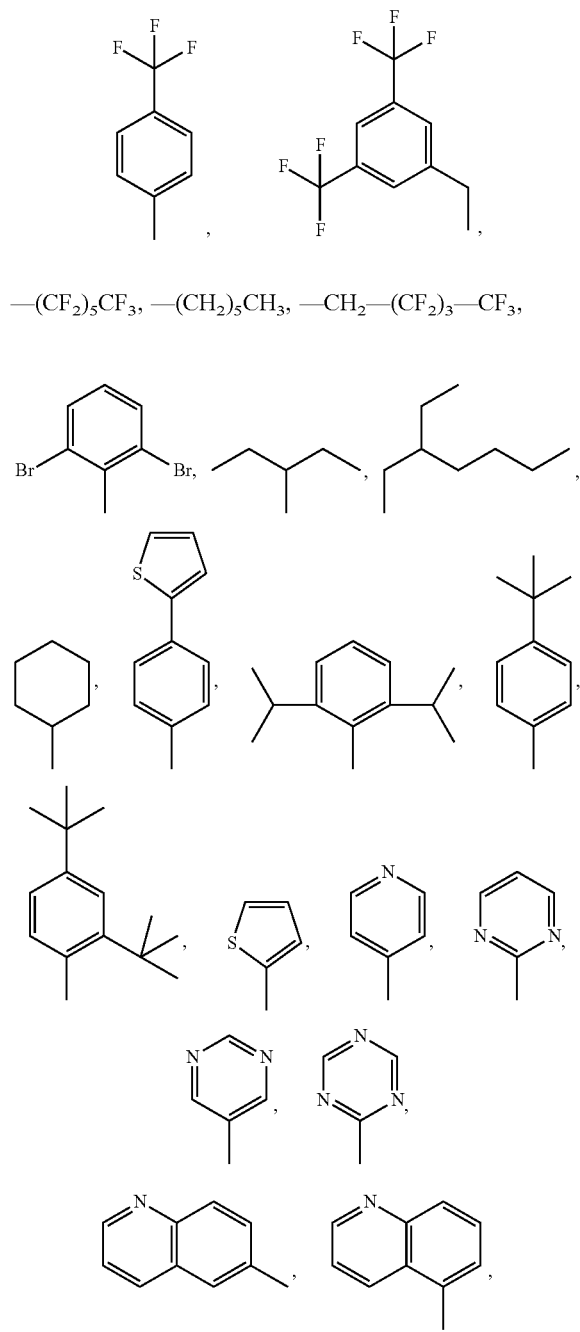
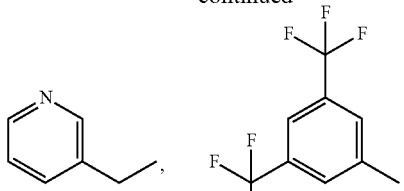
and
$R_1$ is selected from —Br, —H, —OCH$_2$CH$_3$,
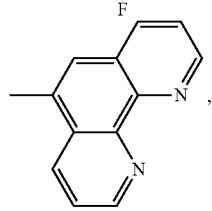
and
Bridge is, preferably, selected from -continued

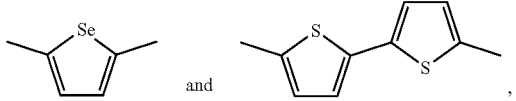
and

As discussed above, the present disclosure provides a transparent N or P or ambipolar material, including a naphthalene diimide (NDI)-based molecule of the present disclosure or a naphthalene diimide dimer (NDI-NDI)-based molecule of the present disclosure.

As discussed above, the present disclosure provides a transparent N material including a naphthalene diimide (NDI)-based molecule of the present disclosure or a naphthalene diimide dialer (NDI-NDI)-based molecule of the present disclosure.

The transparent N material according to the present disclosure preferably has the quality when included in a P:N heterojunction or bilayer or multilayer junction preferably a P1:P2:N1:N2 or P1:P2:N or P:N1:N2 heterojunction or multilayer junction, to dissociate efficiently the excitons created on colored P or a mixture of colored P materials (P1:P2) or of another colored N or mixture of colored N and P materials (P:N2 or P1:P2:N2:) via a process of LUMO dissociation.

According to the present disclosure, the transparent N material accepts electron from the excited state of the donor (the P materials) or the N material(s) absorbing photons)).

According to the present disclosure "transparent" refers to tut absorption coefficient of less than about 60,000 cm$^{-1}$ in the visible wavelength range (about 400 to about 700 nm), and colored refers to an absorption coefficient of more than about 60,000 cm$^{-1}$ in the visible wavelength range with blue, green and red maximum, namely in the region from about 400 nm to about 700 nm (with maxima anywhere in this region or absorbing everywhere in this region).

In one embodiment, the transparent N and/or P or ambipolar material of the present disclosure
exhibits no or very low absorption in the visible wavelength range (about 400 to about 700 nm), i.e. has air absorption coefficient of less than about 60,000 cm$^{-1}$ in the visible wavelength range (about 400 to about 700 nm),
is an organic based compound forming high quality homogenous films when using deposition methods (vaccum deposition or spincoating).

As discussed above, the present disclosure provides a P:N heterojunction or a bi(multi) layer junction, preferably a P1:P2:N1:N2 heterojunction or multilayer junction, including
a naphthalene diimide (NDI)-based molecule or a naphthalene diimide dimer (NDI-NDI)-based molecule according to the present disclosure, or
a transparent N and/or P or ambipolar material according to the present disclosure.

In one embodiment, a transparent N material according to the present disclosure is the acceptor in a P:N heterojunction. See, for example, FIG. 4.

In one embodiment of a P1:P2:N1:N2 heterojunction, one of the P materials could be a transparent P material according to the present disclosure and a donor, as well as one of the N materials could be a transparent N material according to the present disclosure and an acceptor.

In one embodiment, the P:N heterojunction, preferably the P1:P2:N1:N2 heterojunction includes a further N and/or P material,
wherein the further N and/or P material preferably exhibits absorption in the visible wavelength range (about 400 to about 700 nm).

As discussed above, the present disclosure provides the use of a naphthalene diimide (NDI)-based molecule or a naphthalene diimide dimer (NDI-NDI)-based molecule according to the present disclosure, or
a transparent N and/or P or ambipolar material according to the present disclosure in an absorption layer.

In one embodiment, the absorption layer includes a further N and/or P material, wherein the further N and/or P material preferably exhibits absorption in the visible wavelength range (about 400 to about 700 nm).

As discussed above, the present disclosure provides the use of a naphthalene diimide (NDI)-based molecule or a naphthalene diimide dimer (NDI-NDI)-based molecule according to the present disclosure, or
a transparent N and/or P or ambipolar material according to the present disclosure
in a photoelectric conversion layer, and/or
in an organic and/or hybrid module
for optoelectronic application, such as image sensor, photodiode, organic photovoltaics. including organic photoelectric conversion layer(s), OLED and OTFT organic modules, In one embodiment, the photoelectric conversion layer and/or the organic and/or hybrid module includes a further N and/or P material,
wherein the further N and/or P material preferably exhibits absorption in the visible wavelength range (about 400 to about 700 nm)

As discussed above, the present disclosure provides a photoelectric conversion layer including
a naphthalene diimide (NDI)-based molecule or a naphthalene diimide dimer (NDI-NDI)-based molecule according to the present disclosure, or
a transparent N and/or P or ambipolar material according to the present disclosure.

In one embodiment, the photoelectric conversion layer includes a further N and/or P material, wherein the further N and/or P material preferably exhibits absorption in the visible wavelength range (about 400 to about 700 nm).

In one embodiment, the photoelectric conversion layer includes further molecule(s).

As discussed above, the present disclosure provides an absorption layer including a naphthalene diimide (NDI)-based molecule or a naphthalene diimide dimer (NDI-NDI)-based molecule according to the present disclosure, or
a transparent N and or P or ambipolar material according to the present disclosure.

In one embodiment, the absorption layer includes a further N and/or P material, wherein the further N and/or P material preferably exhibits absorption in the visible wavelength range (about 400 to about 700 nm).

In one embodiment, the absorption layer includes further molecule(s).

As discussed above, the present disclosure provides a device, including naphthalene diimide (NDI)-based molecule(s) or naphthalene diimide dimer (NDI-NDI)-based molecule(s) according to the present disclosure, or transparent N and or P or ambipolar material(s) according to the present disclosure or photoelectric conversion layer(s) according to the present disclosure.

Said device can be an organic image sensor, a hybrid image sensor, photodiode, organic photovoltaics, organic light-emitting diode (OLED), organic thin-film transistor (OTFT).

In one embodiment, said photoelectric conversion layer exhibits photo response in the visible absorption range.
In this embodiment, the photoelectric conversion layer of the device includes naphthalene diimide (NDI)-based molecule(s) or naphthalene diimide dimer (NDI-NDI)-based molecule(s) according to the present disclosure or the transparent N and or P or ambipolar material(s) according to the present disclosure and further N and/or P material(s), preferably exhibiting absorption in the visible wavelength range (about 400 to about 700 nm).

According to the present disclosure, when the active materials are (almost) transparent
which gives the following possibilities:
Tuning overall absorption spectrum via tuning absorption of the partner p (the donor) active material only
Tuning of exciton diffusion efficiencies of the partner (absorbing) material only
Tuning of charge generation efficiencies through LUMO only (or almost)
Tuning of only electron mobility
Generally: decoupling of absorption properties in the visible range from electron/hole transfer and transport properties.

In one embodiment, photoelectric conversion layer of the device includes further molecule(s).
The photoelectric conversion layer can include different components (dyes) and combinations thereof.

In one embodiment, the photoelectric conversion layer and/or the absorption layer includes further n and p type materials (molecules) that can be used together with the material(s) of the present disclosure, such as
phthalocyanine (Pc), subphthalocyanine (SubPc), merocyanine (MC), diketopyrrolopyrroles (DPP), borondipyrromethene (BODIPY), isoindigo (ID), perylene diimides (PDI), and quinacridone (QD), fused acenes, such as pentacene and tetracene and triphenylamine (TPA) as donor (absorbing p materials).

As discussed above, the present disclosure provides an organic image sensor, including photoelectric conversion layoffs) according to the present disclosure.
The organic image sensor of the present disclosure preferably includes
(a) an organic photoelectric conversion unit including photoelectric conversion layer(s) according to the present disclosure,
(b) at least one electrode,
(c) a substrate,
(d) optionally, a second electrode on top of said photoelectric conversion layer(s).

The substrate can be silicon, quartz, glass, polymer, such as PMMA, PC, PS, COP, COP, PVA, PVP, PES, PET, PEN, mica, or combinations thereof.
The substrate can also be other photoelectric conversion unit(s).
This means, a device of this disclosure can include (i) two inorganic units with one organic unit, (ii) one inorganic unit with two organic units, or (iii) three organic units combined with each other in the organic image sensor. Any of the organic units can contain molecules/layers/devices according to this disclosure.

In a preferred embodiment, an organic image sensor consists of three organic conversion units containing molecules in layers as of this disclosure (in devices, each with transparent electrodes), combined with each other and operating each in one of the ranges 400 nm to 500 nm, 500 nm to 600 nm and 600 nm to 700 nm.

Combined units can be realized either by vertical and/or horizontal stacking of the organic-organic or organic-inorganic units.
The electrode material can be
transparent metal oxide, such as indium tin oxide (ITO), fluorine-doped indium oxide (IFO), tin oxide, fluorine-doped tin oxide (FTO), antimonium-doped tin oxide (ATO), zinc oxide (including Al, B and Ga doped zinc Oxide), indium oxide-zinc oxide (IZO), $TiO_2$,
non transparent or semitransparent metal or alloy or conductive polymer, such as Au, Ag, Cr, Ni, Pd, AlSiCu, or any metal or metal alloy or metal combination with suitable workfunction; PEDOT/PSS, PANI or PANI/PSS, graphene.

As discussed above, the present disclosure provides a hybrid Silicon-organic image sensor or organic image sensor, including
(a) an organic photoelectric conversion unit or units including photoelectric conversion layer(s) according to the present disclosure.
(b) optionally, a Si based photoelectric conversion unit,
(c) metal wiring,
(d) a (CMOS) substrate.
(e) insulating layer(s), preferably oxide.

In one embodiment, said organic photoelectric conversion unit of the image sensors of the present disclosure includes different layers within the organic based photoelectrical conversion unit(s), such as
n-type material,
p-type material,
n-buffer layer,
p-buffer layer.
or combinations and or mixtures (e.g. n material and p material co-deposited in one layer) thereof.

For example, the organic image sensor of the present disclosure can have the structure:
substrate/first electrode/n-buffer layer/n-material/p-material/p buffer layer/second electrode;
substrate/first electrode/n-buffer layer/n-material/mixture of n- and p-material/p-material/p buffer layer/second electrode;
substrate/first electrode/n-buffer layer/n-material/mixture of n- and p-material p buffer layer/second electrode;
substrate/first electrode/p-buffer layer/p-material/n-material/n buffer layer/second electrode.
substrate/first electrode/p-buffer layer/p-material/ mixture of n- and p-material/n-material/n buffer layer/second electrode.
substrate/first electrode/p-buffer layer/p-material/ mixture of n- and p-material/n buffer layer/second electrode.

The organic image sensor of the present disclosure can include different layer structures, in particular regarding the position of the n and p material with respect to the CMOS part.

The organic photoconversion unit can be used in combination with a Si based photoelectrical conversion unit where different layers absorb different color (BGR) in a hybrid silicon-organic image sensor (see FIG. 2) or can be used without Si based photoelectrical conversion unit. In this case the organic photoconversion unit has the capability of absorbing different color (BGR) (see FIG. 3).

The BGR ranges are 400-500 nm, 500-600 nm and 600-700 nm and the absorption outside of the range is preferably less than 20%, more preferably less titan 10 and 5%.

As discussed above, the substrate can also be other photoelectric conversion unit(s).

As discussed above, a device of this disclosure can include (i) two inorganic units with one organic unit, (ii) one inorganic unit with two organic units, or (iii) three organic units combined with each other in the organic image sensor. Any of the organic units can contain molecules/layers/devices according to this disclosure.

The deposition methods to produce the organic photo-electrical conversion layer are PVD, CVD, spin coating, dipping coating, casting process, inkjet printing, screen printing, spray coating, offset printing.

Different process temperatures for processing the layer are possible, namely from 150 to 445° Celsius.

As discussed above, the present disclosure provides a method for synthesis of transparent n materials, in particular, naphthalene diimide (NDI)-based materials (such as of general formula I) including the step(s) of imidization of 2,6-dibromonaphthalene-1,4,5,8-tetracarboxylic dianhydride derivatives in the presence of a R-primary amine and acid, followed by the palladium catalyzed Suzuki Coupling with the specific R1-boronic ester.

The present disclosure provides also a method for synthesis of naphthalene diimide dimer (NDI dimer)-based materials, including (i) in the case of general formula II the steps of mono imidization of 2,6-dibromonaphthalene-1,4,5,8-tetracarboxylic dianhydride derivatives in the presence of a R-primary amine and acid, followed by a second imidization in the presence of a "Bridge"-diamine and acid, and (ii) in the case of general formula III the steps of imidization of 2,6-dibromonaphthalene-1,4,5,8-tetracarboxylic dianhydride derivatives in the presence of a R-primary amine and acid, followed by a mono palladium catalyzed Suzuki Coupling with the specific R1-boronic ester, followed by a second palladium catalyzed Suzuki Coupling with the specific Bridge-diboronic ester.

Note that the present technology can also be configured as described below.

(1) A naphthalene diimide (NDI)-based molecule represented by the general formula I

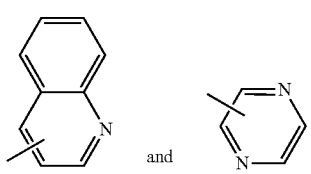

wherein

R is, at each occurrence, independently selected from $-C_xH_{2x+1}$, $-C_xX_{2x+1}$, $-C_xH_2X_{2x-1}$,

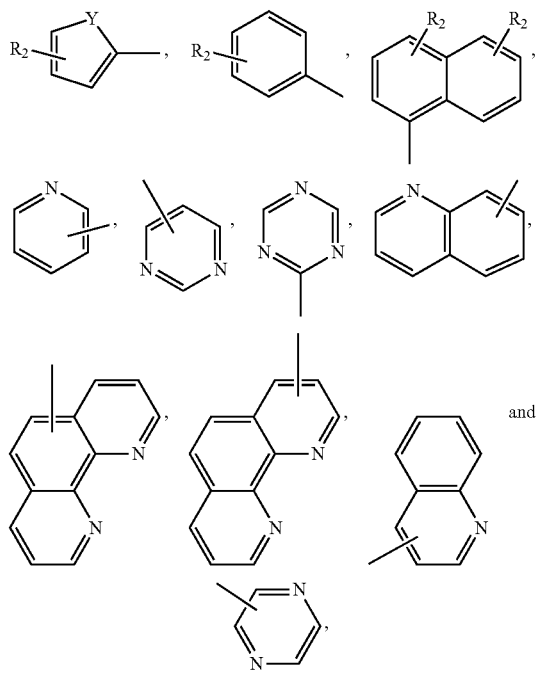

$R_1$ is, at each occurrence, independently selected from

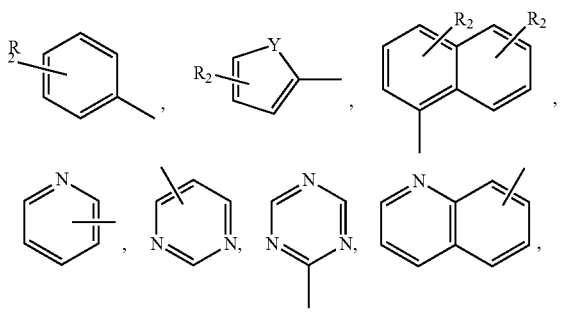

x is an integer from 1 to 10,

X is halogen (F, Cl, Br, I),

Y is selected from $CH_2$, S, O, Se and $N-R_2$, $R_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group.

(2) The naphthalene diimide (NDI)-based molecule of (1), wherein
R is selected from
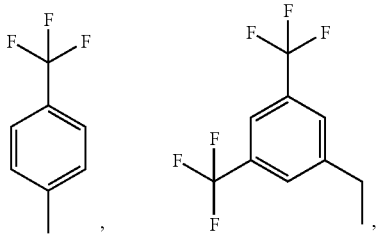 [SMILES: Cc1ccc(C(F)(F)F)cc1 ; CCc1cc(C(F)(F)F)cc(C(F)(F)F)c1]
—(CF$_2$)$_5$CF$_3$, —(CH$_2$)$_5$CH$_3$, —CH$_2$—(CF$_2$)$_3$—CF$_3$,
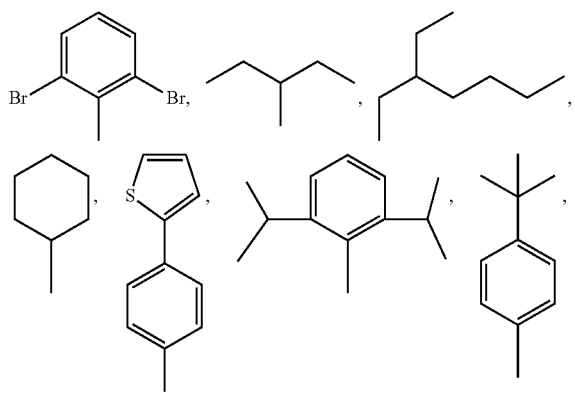
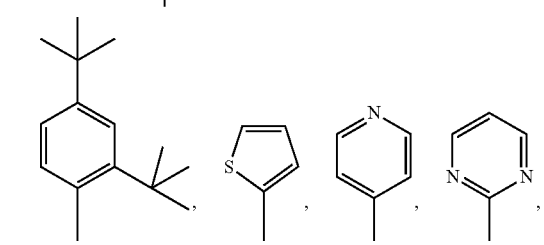
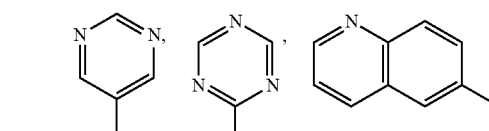
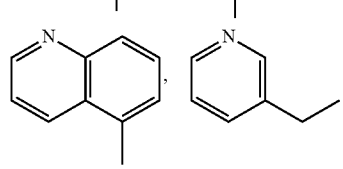
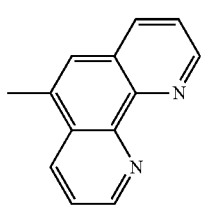
and
R$_1$ is selected from
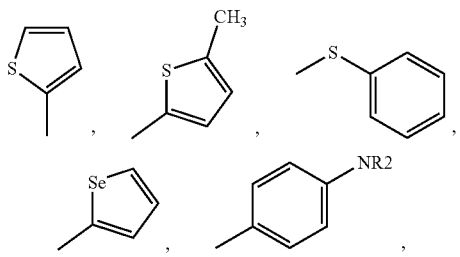
—OCH$_2$CH$_3$, —Br, —H,
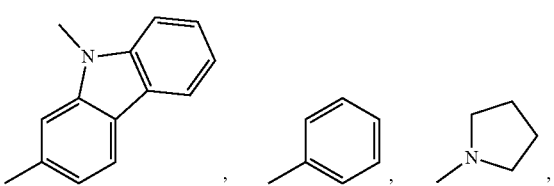
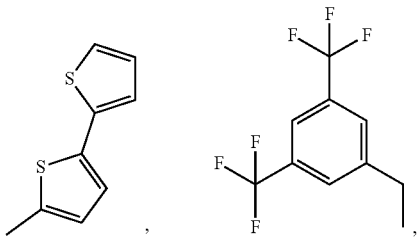
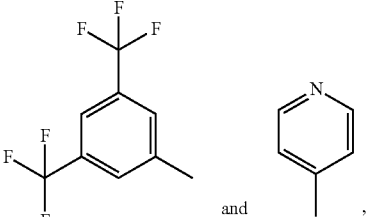
wherein preferably
R is
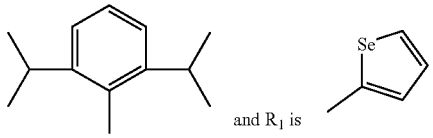
and R$_1$ is (3) A naphthalene diimide (NDI)-based molecule represented by the general formula Ia
wherein

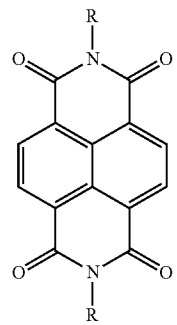

Ia

R is, at each occurrence, independently selected from —$C_xH_{2x+1}$, —$C_xX_{2x+1}$, —$C_xH_2X_{2x-1}$,

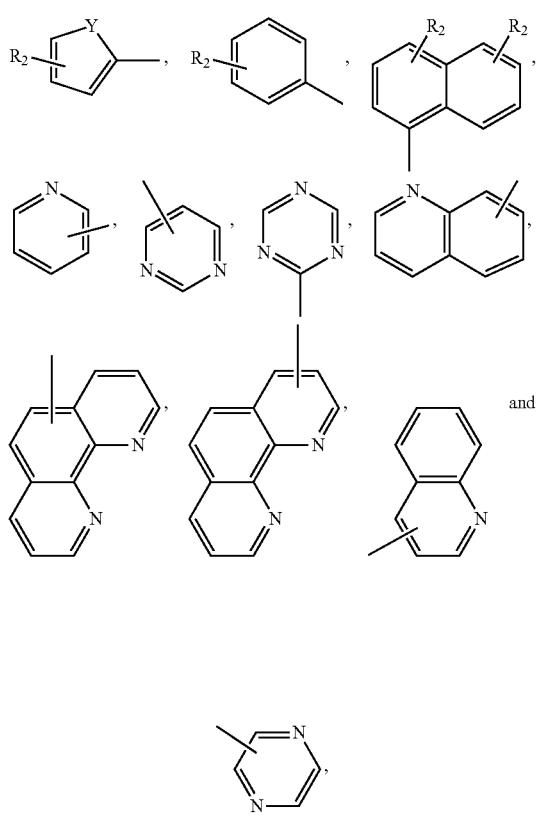

and x is an integer from 1 to 10,

X is halogen (F, Cl, Br, I),

Y is selected from $CH_2$, S, O, Se and N—$R_2$, $R_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group.

(4) The naphthalene diimide (NDI)-based molecule of (3), wherein

R is selected from

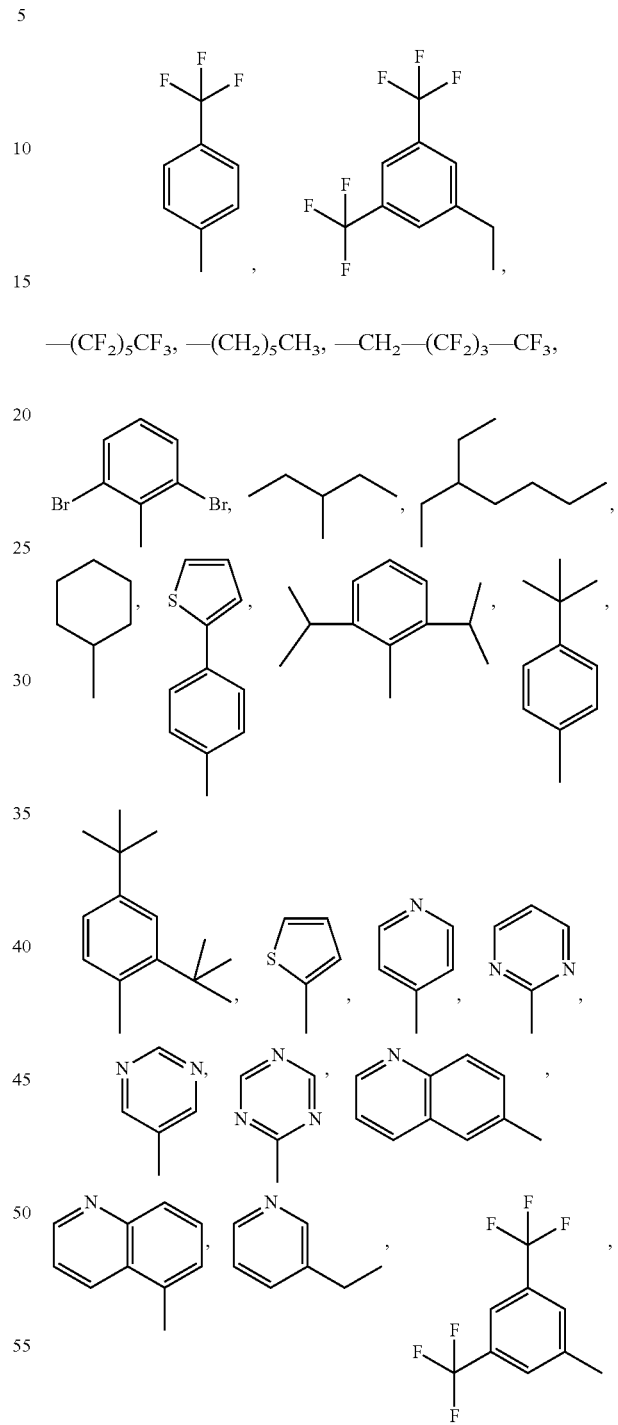

—$(CF_2)_5CF_3$, —$(CH_2)_5CH_3$, —$CH_2$—$(CF_2)_3$—$CF_3$,

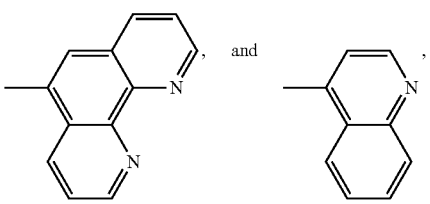

wherein, preferably, R is selected

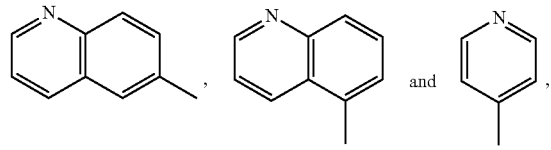

, and , wherein more preferably R is

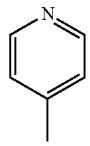

.

(5) The naphthalene diimide dimer (NDI-NDI)-based molecule represented by the general formula II or III

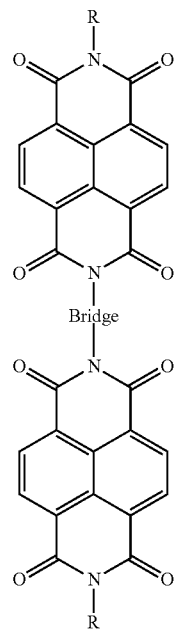

II

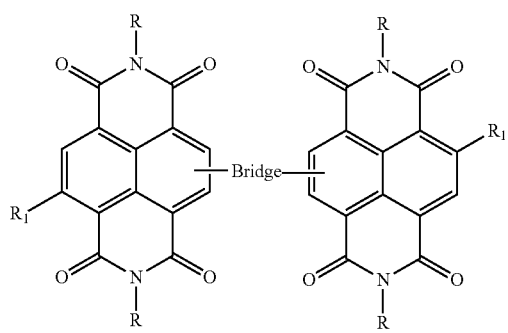

III wherein in general formula II
R is, at each occurrence, independently selected from —$C_xH_{2x+1}$, —$C_xX_{2x+1}$, —$C_xH_2X_{2x-1}$,

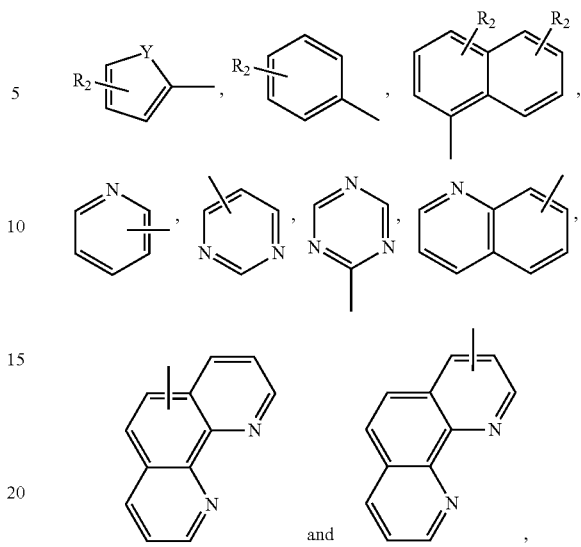

Bridge is selected from

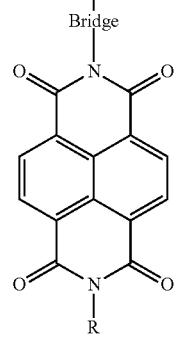

and x is an integer from 1 to 10,
X is halogen (F, Cl, Br, I),
Y is selected from $CH_2$, S, O, Se and N—$R_2$,
$R_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group, and wherein in general formula III
R is, at each occurrence, independently selected from —$C_xH_{2x+1}$, —$C_xX_{2x+1}$, —$C_xH_2X_{2x-1}$,

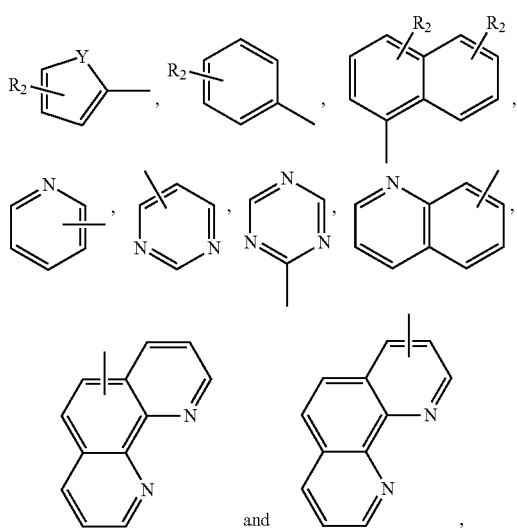

R₁ is, at each occurrence, independently selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated alkyl group, heteroaryl group, fluorenyl group, and Bridge is selected from

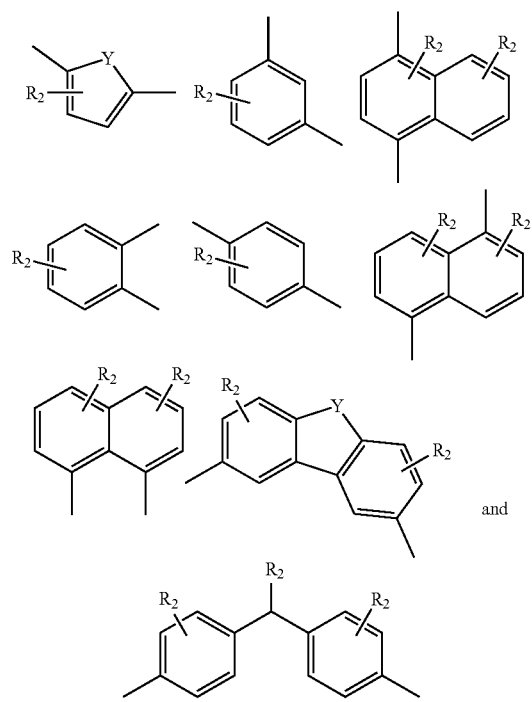

x is an integer from 1 to 10,
X is halogen (F, Cl, Br, I),
Y is selected from CH₂, S, O, Se and N—R₂,
R₂ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group.

(6) The naphthalene diimide dimer (NDI-NDI)-based molecule represented by the general formula II of (5), wherein R is selected from

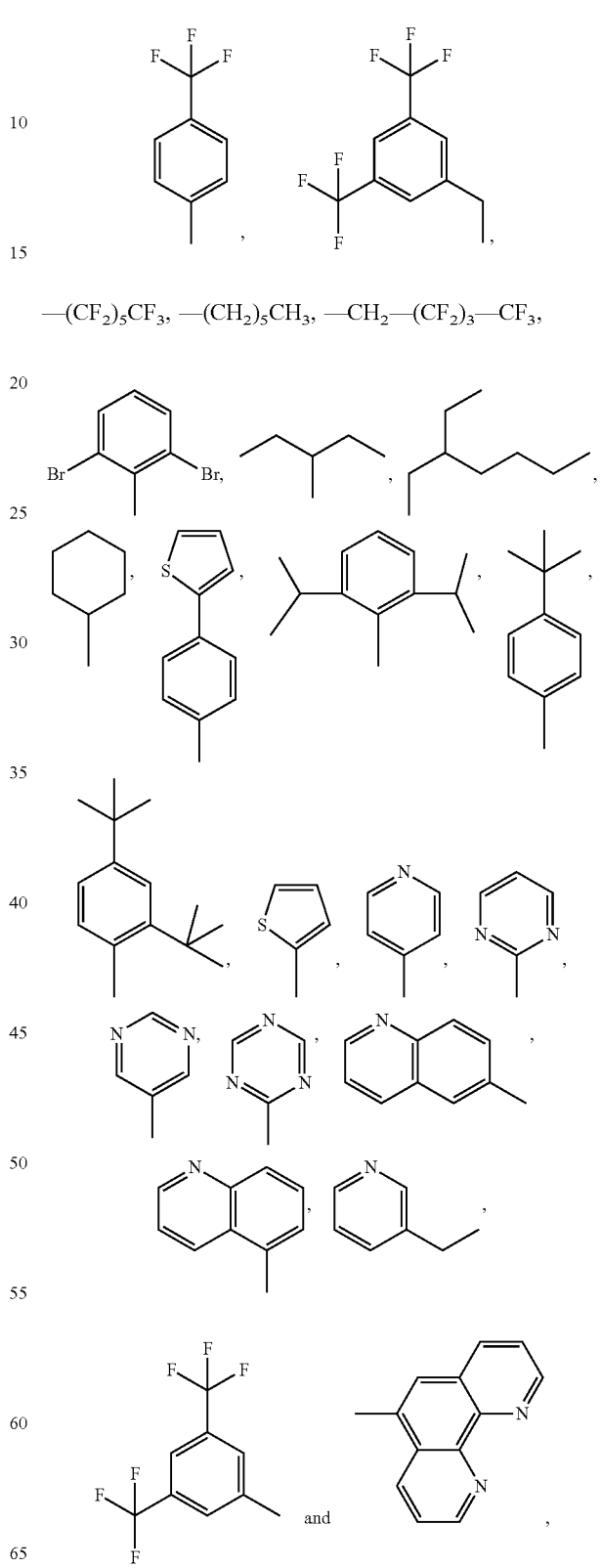

—(CF₂)₅CF₃, —(CH₂)₅CH₃, —CH₂—(CF₂)₃—CF₃, and
Bridge is selected from
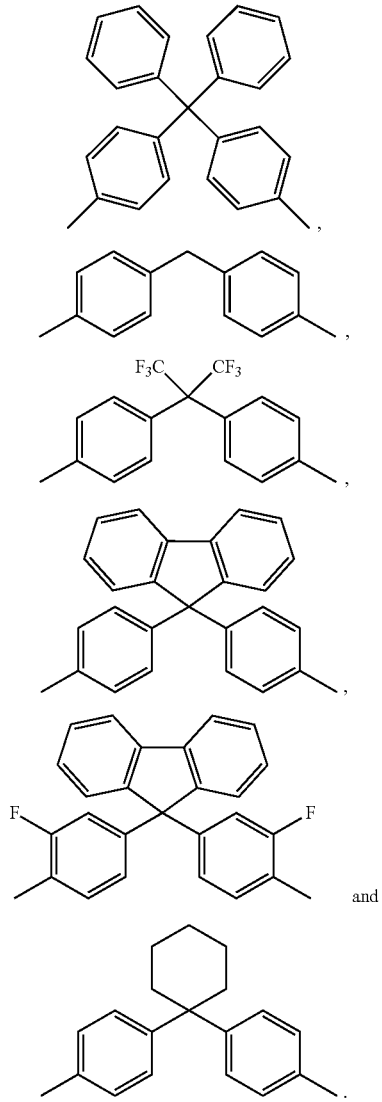
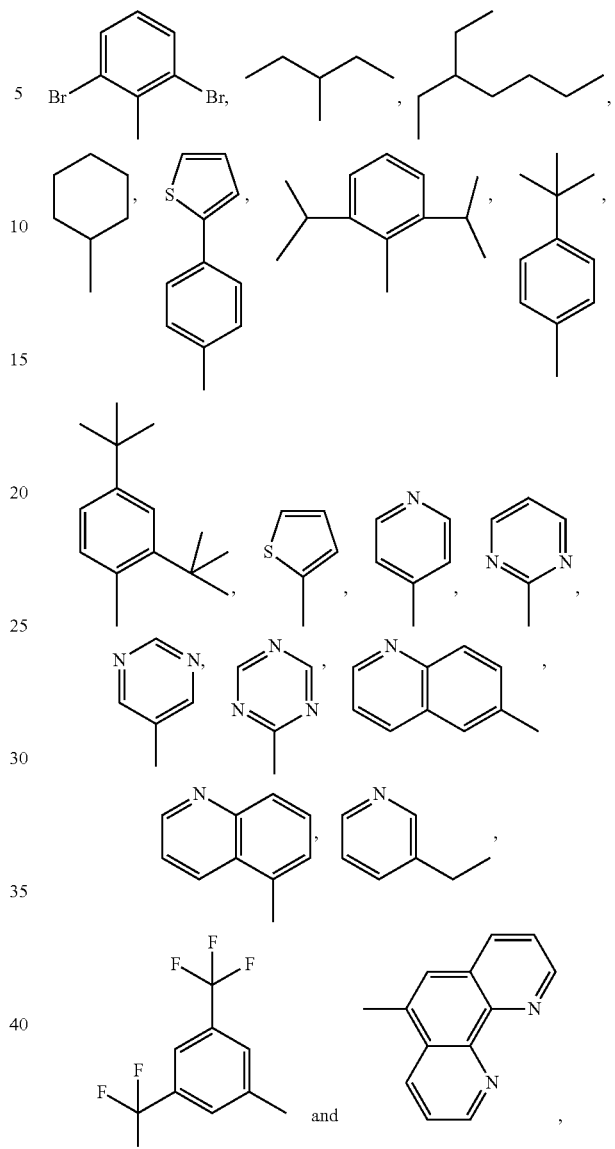
(7) The naphthalene diimide dimer (NDI-NDI)-based molecule represented by the general formula III of (5), wherein R is selected from
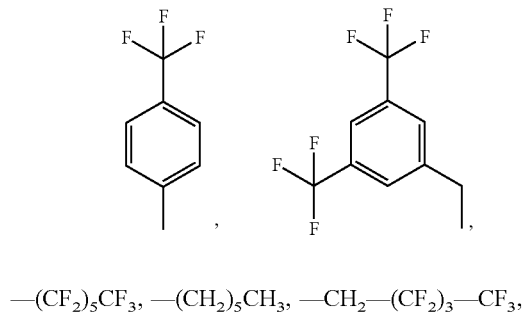
—(CF$_2$)$_5$CF$_3$, —(CH$_2$)$_5$CH$_3$, —CH$_2$—(CF$_2$)$_3$—CF$_3$,
and
R$_1$ is selected from —Br, —H, —OCH$_2$CH$_3$,
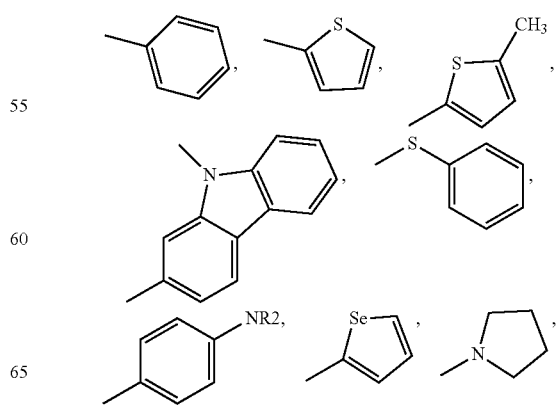

-continued

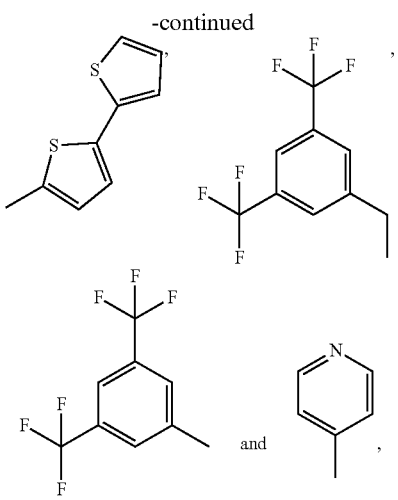

and
Bridge is, preferably, selected from

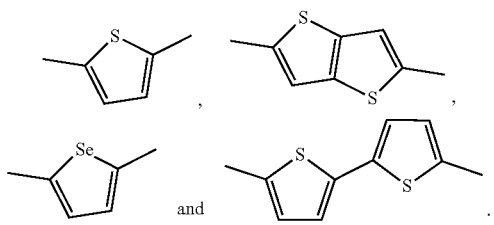

(8) A transparent N or P or ambipolar material, including a naphthalene diimide (NDI)-based molecule or a naphthalene diimide dimer (NDI-NDI)-based molecule of any one of (1) to (7).
(9) The transparent N or P ambipolar material of (8), wherein the material
has art absorption coefficient of less than about 60,000 cm$^{-1}$ in the visible wavelength range (about 400 to about 700 nm),
is an organic based compound forming high quality homogenous films when using deposition methods (vaccum deposition or spincoating).
(10) A P:N heterojunction or a bi(multi) layer junction, preferably a P1:P2:N1:N2 heterojunction or multilayer junction, including
a naphthalene diimide (NDI)-based molecule or a naphthalene diimide dimer (NDI-NDI)-based molecule of any one of (1) to (7), or
a transparent N and/or P or ambipolar material according to (8) or (9),
optionally including a further N and/or P material,
wherein the further N and/or P material preferably exhibits absorption in the visible wavelength range (about 400 to about 700 nm).
(11) Use of a naphthalene diimide (NDI)-based molecule or a naphthalene diimide dimer (NDI-NDI)-based molecule of any one of (1) to (7),
7 or of a transparent N and or P or ambipolar material according to (8) or (9) in an absorption layer,
optionally including a further N and/or P material,
wherein the further N and/or P material preferably exhibits absorption in the visible wavelength range (about 400 to about 700 nm).
(12) Use of a naphthalene diimide (NDI)-based molecule or a naphthalene diimide dimer (NDI-NDI)-based molecule of any one of (1) to (7), or of a transparent N and/or P or ambipolar material according to (8) or (9), in a photoelectric conversion layer and/or in an organic and/or hybrid module for optoelectronic application, such as image sensor, photodiode, organic photovoltaics, including organic photoelectric conversion layer(s), OLED and OTFT organic modules, optionally including a further N and/or P material, wherein the further N and/or P material preferably exhibits absorption in the visible wavelength range (about 400 to about 700 nm).
(13) A photoelectric conversion layer including a naphthalene diimide (NDI)-based molecule or a naphthalene diimide dimer (NDI-NDI)-based molecule of any one of (1) to (7). or a transparent N and/or P or ambipolar material according to (8) or (9),
optionally including a further N and/or P material,
wherein the further N and/or P material preferably exhibits absorption in the visible wavelength range (about 400 to about 700 nm)
and optionally including further molecule(s).
(14) An absorption layer including a naphthalene diimide (NDI)-based molecule or a naphthalene diimide dimer (NDI-NDI)-based molecule of any one of (1) to (7), or a transparent N and/or P or ambipolar material according to (8) or (9),
optionally including a further N and/or P material, and
optionally including further molecule(s).
wherein the further N and/or P material preferably exhibits absorption in the visible wavelength range (about 400 to about 700 nm).
(15) A device, including naphthalene diimide (NDI)-based molecule(s) or naphthalene diimide dimer (NDI-NDI)-based molecule(s) of any one of (1) to (7), or transparent N and/or P or ambipolar material(s) according to (8) or (9), or photoelectric conversion layer(s) according to (13),
wherein said device is preferably an organic image sensor, an hybrid image sensor, photodiode, organic photovoltaics, organic light-emitting diode (OLED), organic thin-film transistor (OTFT).
(16) The device according to (15), wherein said photoelectric conversion layer exhibits photo response in the visible absorption range.
(17) The device according (15) or (16), including naphthalene diimide (NDI)-based molecule(s) or naphthalene diimide dimer (NDI-NDI)-based molecule(s) of any one of (1) to (7), or transparent N and or P or ambipolar material(s) according to (8) or (9), or photoelectric conversion layer(s) according to (13),
and/or including further N and/or P material(s) preferably exhibiting absorption in the visible wavelength range (about 400 to about 700 nm),
and/or including further molecule(s).
(18) An organic image sensor, including
(a) an organic photoelectric conversion unit including photoelectric conversion layer(s) according to (13),
(b) at least one electrode,
(c) a substrate,
(d) optionally, a second electrode on top of said photoelectric conversion layer(s).
(19) A hybrid Silicon-organic image sensor or organic image sensor, including
(a) an organic photoelectric conversion unit or units including photoelectric conversion layer(s) according to (13),
(b) optionally, a Si based photoelectric conversion unit,
(c) metal wiring, (d) a (CMOS) substrate,
(e) insulating layer(s), preferably oxide.
(20) The organic image sensor according to (18) or (19), wherein said organic photoelectric conversion unit includes different layers,
such as n-type material, p-type material, n-buffer layer and/or p-buffer layer or combinations or mixtures thereof.
(21) A method for synthesis of transparent n materials, in particular, naphthalene diimide (NDI)-based materials (such as of general formula I) including the step(s) of
imidization of 2,6-dibromonaphthalene-1,4,5,8-tetracarboxylic dianhydride derivatives in the presence of a R-primary amine and acid,
followed by the palladium catalyzed Suzuki Coupling with the specific R1-boronic ester.
(22) A method for synthesis of naphthalene diimide dimer (NDI dimer)-based materials, preferably of general formula II, including the steps of
mono imidization of 2,6-dibromonaphthalene-1,4,5,8-tetracarboxylic dianhydride derivatives in the presence of a R-primary amine and acid,
followed by a second imidization in the presence of a "Bridge"-diamine and acid.
(23) A method for synthesis of naphthalene diimide dimer (NDI dimer)-based materials, preferably of general formula III, including the steps of
imidization of 2,6-dibromonaphthalene-1,4,5,8-tetracarboxylic dianhydride derivatives in the presence of a R-primary amine and acid,
followed by a mono palladium catalyzed Suzuki Coupling with the specific R1-boronic ester,
followed by a second palladium catalyzed Suzuki Coupling with the specific Bridge-diboronic ester.

The term "naphthalene diimide" or "NDI" or naphthalene diimide-based material", as used herein, refers to a molecule based on 1,4,5,8-naphthalenediimides structures.

The term "N material", as used herein, refers to refers to a material accepting an electron.

The term "P material", as used herein, refers to refers to a material donating an electron.

The term "ambipolar material", as used herein, refers to a material able to transport both electrons and holes with comparable mobilities.

The term "absorption in the visible wavelength range" or "molecule exhibiting absorption in the visible wavelength range", as used herein, is meant to refer to a molecule/dye that is able to absorb light in only one or several parts of the entire range indicated or over the total range. For example a molecule may only absorb in the range of from 500-700 nm, whereas another molecule may absorb in the range of from 400-700 nm or 500-600 nm, whereas a third molecule may absorb over the range of from 400-500 nm (or the above described sub-ranges of preferably 400 nm to 500 nm, or 500 nm to 600 nm, or 600 nm to 700 nm). All these scenarios are meant to be encompassed by such wording.

The term "narrow absorption band", as used herein, is meant to refer to/means that the width of the absorption band at 0 intensity is 200 nm , more preferably 150 nm, more preferably 100 nm.

The term "transparent" or "transparent material", as used herein, refers to a material having an absorption coefficient of less than about 60,000 $cm^{-1}$ or an extinction coefficient of less than about 60,000 $M^{-1}cm^{-1}$ (in toluene) in the visible wavelength range (about 400 to about 700 nm).

The term "colored" or "colored material", as used herein, refers to a material having an absorption coefficient of more than about 60,000 $cm^{-1}$ in the visible wavelength range with blue, green or red maximum, in particular in the region from about 400 nm to about 700 nm (with maxima anywhere in this region or absorbing everywhere in this region).

In accordance with the present disclosure, the term "electrode" refers to an electrical lead to apply voltage. An electrode may be "interdigitated", meaning that it has a comb-like shape with two combs lying opposite each other and the respective figures of the combs engaging with each other. Alternatively, an electrode may be a non-interdigitated. An electrode may be transparent or non-transparent. A transparent electrode may, for example, be formed from indium tin oxide (ITO) or from fluorinated tin oxide (FTO). A non-transparent electrode may be reflective and may, for example, be formed from silver (Ag) or gold (Au).

The requirements of a photoelectric conversion layer to be used in image sensors are demanding and can be summarised as followed:
(i) narrow absorption band of at least one active material;
(ii) high extinction coefficient, $\varepsilon > 10^4$ L $mol^{-1}cm^{-1}$—correspondingly high absorption coefficient of at least one active material:
(iii) heat resistant;
(iv) high photoelectric conversion efficiency (EQE);
(v) high-speed responsivity/high charge carrier mobility;
(vi) low dark-current in device;
(vii) thin film by thermal vapour deposition (Tvp<Tdec).

The present inventors have found—for the use as active materials for the organic photoconversion unit—material of specific structure which no or very low absorption in the visible range (400 to 650 nm), belonging to the following different families;
Naphthalene dimides (NDI) and
Dimers of Naphthalene dimides.

Said materials are used in a bulk heterojunction (mixed p-n layer) or PN heterojunction (formed between a p layer and n layer or PiN junction (p layer—mixed layer as p-n bulk heterojunction—n-layer) in the photoelectric conversion material layer together with a material that absorbs in the visible range.

The materials of the present disclosure can be used as active materials for the organic photoconversion unit.

The organic photoconversion unit can be used in combination with a Si based photoelectrical conversion unit where different layer absorbed different colour (BGR) in a hybrid Silicon-organic image sensor or can be used without Si based photoelectrical conversion unit. In this case the organic photoconversion unit having the capability of absorbing different colour (BGR).

Figure 2:
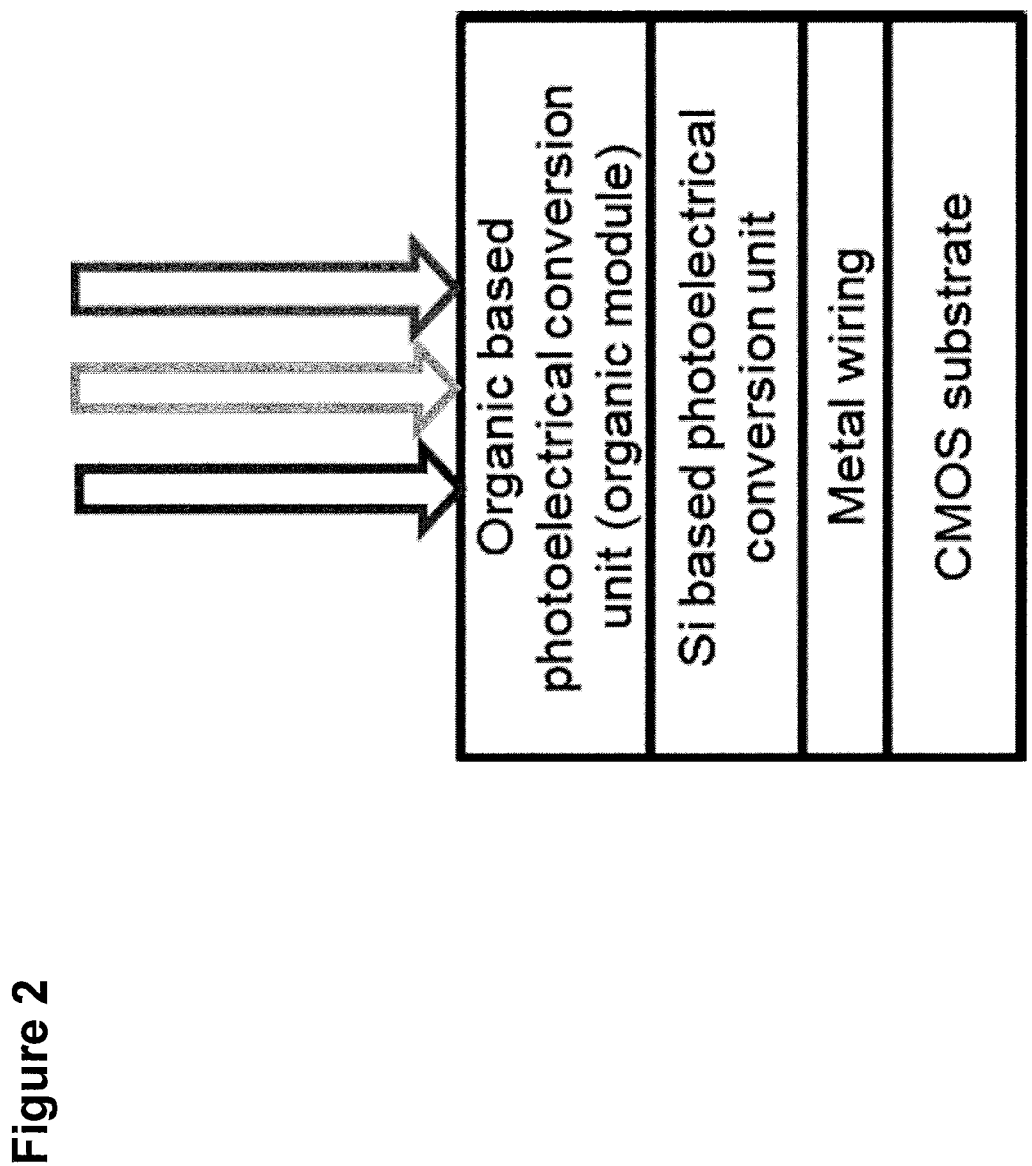
FIG. 2 shows a schematic representation of the hybrid silicon-organic image sensor.
Figure 3:
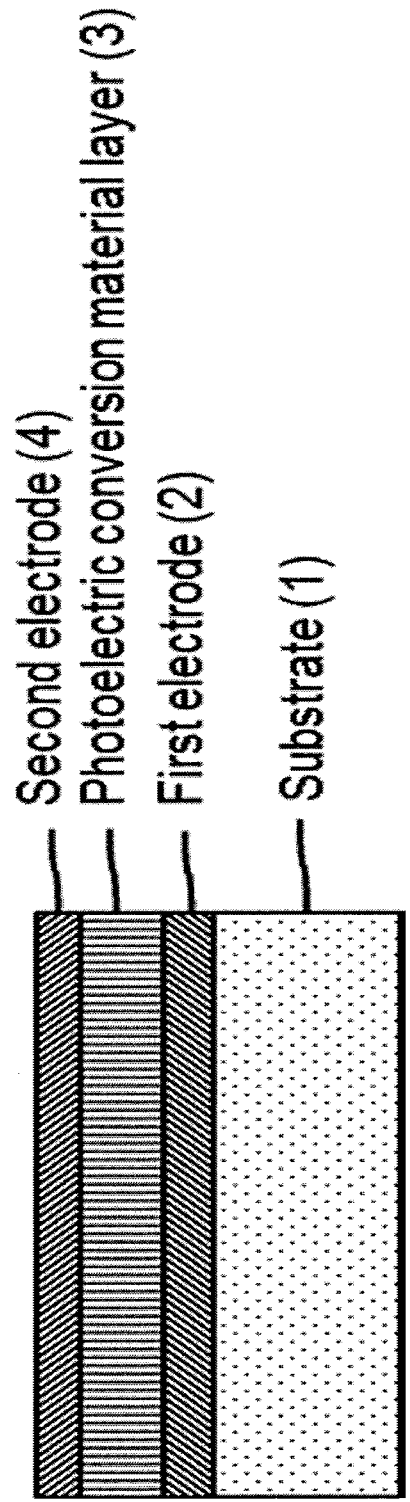
FIG. 3 shows a schematic representation of the organic based photoelectrical conversion unit with the different layers.

The general structure of the resulting hybrid image sensor device as well as the details of the organic based photoelectrical conversion unit are schematic represented in the FIGS. 2 and 3.

The present inventors have found a transparent N or a transparent P material (transparent=400 nm to 700 nm absorption coefficient of films <60000 $cm^{-1}$ or extinction coefficient (in toluene)<60,000 $M^{-1}cm^{-1}$) and which in devices with P:N (generally P1:P2:N1:N2) heterojunctions can.

If N—dissociate efficiently the excitons created on the coloured (coloured=absorption coefficient in Vis is >60 000 in the VIS region with blue, green or red maximum) P (or the mixture of coloured P materials) or of another coloured N (or mixture of coloured N materials) via the process of LUMO dissociation—accepting electron from the excited state of the donor (the P materials) or the N material(s) absorbing photons))

Figure 4:
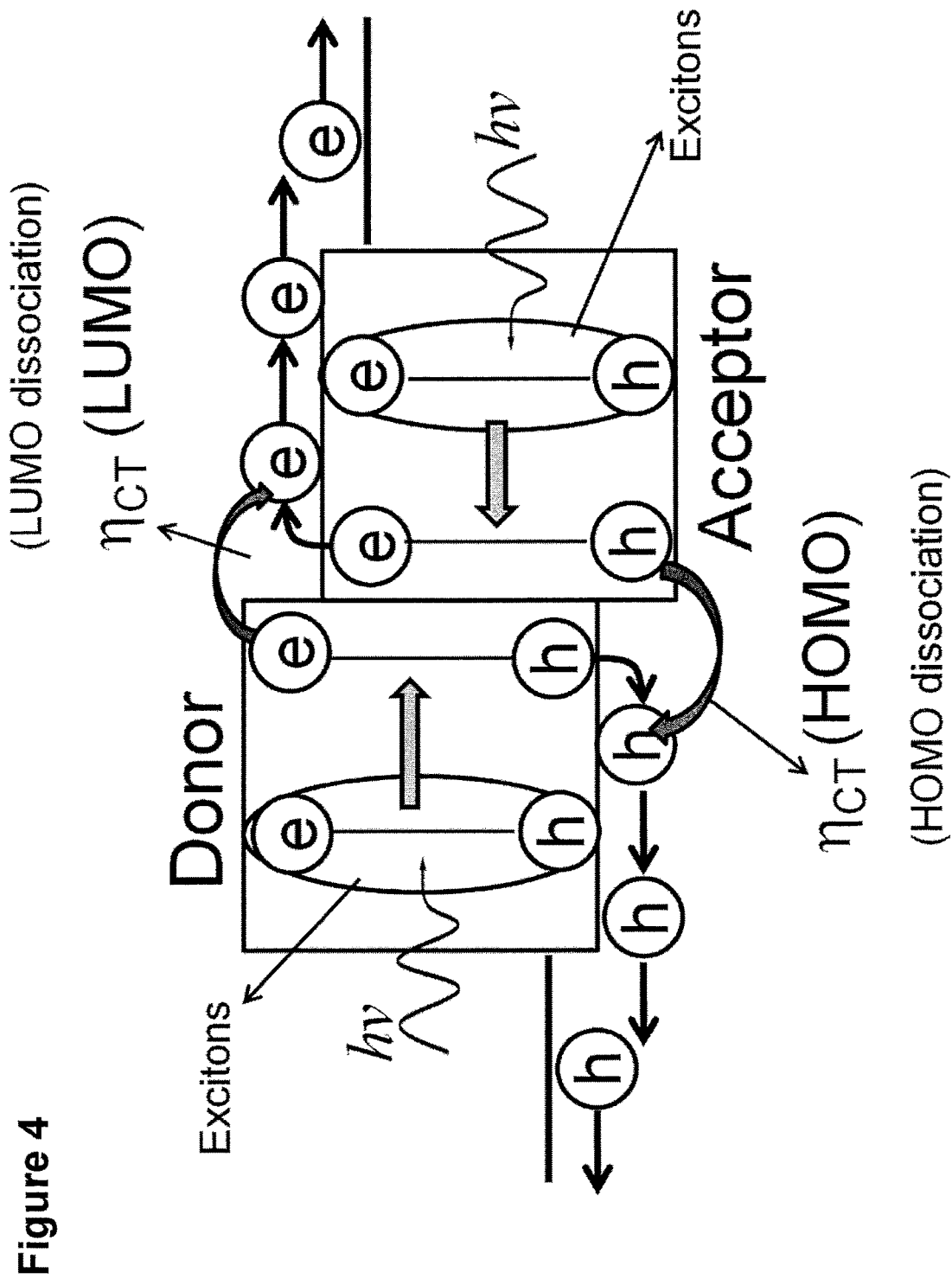
FIG. 4 describes the HOMO and LUMO dissociation process.

If P—dissociate efficiently the excitons created on the coloured (coloured=absorption coefficient in VIS is >60 000 in the VIS region with blue, green or red maximum) N (or the mixture of coloured N materials) or of another coloured P (or mixture of coloured P materials) via the process of HOMO dissociation—donating electron into the HOMO of the excited coloured material (the P material(s) or the N material(s) absorbing photons)) which is equivalent to accepting a hole from them For example, in a P:N example the P material is the donor and the N material the Acceptor (as e.g. shown in FIG. 4). In an embodiment, where P1:P2:N1:N2: one of the N materials could be a Donor as well one of the P materials could be an acceptor Dissociation/charge transfer efficiency ($\eta CT$) general description:

$\eta CT$ has $\eta CT(HOMO)$ and $\eta CT(LUMO)$ parts

In FIG. 4 (as example)

- The Acceptor is the N material accepting an electron—either in its LUMO (transparent N) with $\eta CT(LUMO)$ or in its HOMO (transparent P) state with $\eta CT(HOMO)$ (this last one is equivalent to hole transferred to the donor);
- The Donor is the material donating an electron—from its LUMO (when in excited state=colored P) or from its HOMO (transparent P);
- For transparent N—the $\eta CT(LUMO)$ has to be high;
- For transparent P—the $\eta CT(HOMO)$ has to be high.

The main advantages of the transparent n and/or p materials of the present disclosure, in particular for the application in photoelectrical conversion layers and devices are as follows:

1. The possibility to adjust the absorption spectrum of the active device via adjusting the absorption spectrum of only one active component. This will be the spectrum of the partner material—the p partner material absorption when using transparent n materials and n partner materials absorption when using transparent p materials.
2. Possibility for tuning the electron mobility only in transparent n materials and the hole mobility only of transparent p materials
3. HOMO or LUMO level tuning (together with ensuring large band gap for high transparency in the visible range.
4. Possibility for optimising one exciton dissociation/charge generation efficiency only—either through the LUMO (for transparent n) or through the HOMO (for transparent p materials (see FIG. 4).

The main advantages of the new n and p materials without absorption or with a very low absorption in the visible wavelengths (400-700 nm) as active materials for the application in photoelectrical conversion layers are as follows:

- excellent photostability—especially due to UV absorption only;
- possibility for tuning of the absorption spectrum of the device via the absorption of the partner (the other) active component—i.e. the absorption spectrum of p material in case of transparent n and the absorption of n material in case of transparent p:
- easy alteration of HOMO and LUMO energy levels;
- high thermal stability (300 to 500° C. depending on substituents but at least 300° C.);
- high electrons (for n) and/or holes (for p) mobilities—especially the independent tuning of mobilities—e.g. only high electrones mobility for transparent n material is needed;
- high exciton dissociation ability—to allow for photoconversion devices with high EQE;
- high charge generation efficiencies of the devices—high charge transfer efficiency and charge separation efficiency;
- especially independent tuning of the charge generation efficiency—through the LUMO (for transparent n) and through the HOMO (for transparent p);
- can be used as n-buffer or p-buffer layers correspondingly—allows for further device optimisation via possible tuning of morphology of the active layer and/or energy level alignment through the device.

Further details are disclosed in the parallel European patent application No. 15 161 993.9 filed Mar. 31, 2015 and the parallel PCT application No, PCT/EP2016/057144 filed Mar. 31, 2016.

The main advantages of the naphthalene monoimide (NMI) and naphthalene diimide (NDI) as well as the dimer combinations of this naphthalene based molecules for the application in photoelectrical conversion layers are as follows:

- exhibit excellent photo—and thermal stability (300 to 500°);
- easy alteration of HOMO and LUMO energies is possible;
- very low extinction coefficients in the visible range;
- high electron mobilities;
- in case of dimers:
    - 3D structure and LUMO degeneration which increases dissociation efficiency (LUMO dissociation);
    - higher electron mobilities;
    - give possibility for highly efficient LUMO based dissociation of the excitons formed in the absorbing p partner.

The energy levels and the morphology in thin film are tunable by the type of substituents R, $R_1$ and bridge. This makes the naphthalene monoimide (NMI) and naphthalene diimide (ND) as well as the dimer combinations of this naphthalene based molecules very versatile molecules to be used in the organic photoelectric conversion layer in combination with a material that absorbs in the visible range.

The main advantages of the NDI-based molecules, such as NDI1 with a very low absorption in the visible wavelengths as active materials for the application in photoelectrical conversion layers are as follows:

- exhibit excellent photostability,
- excellent thermal stability (NDI1 up 380, even higher for the dimers),
- very low extinction coefficients in the visible range,
- electron mobilities in the range of $10^{-7}$-$10^{-5}$ (cm²/Vs),
- exciton diffusion efficiencies for different p absorbing partners—up to 90%,
- charge transfer efficiencies for QD and BQD p materials up to 60%,
- Charge separation efficiencies within 1000 ns (for the same p partners)—up to 90%,
- processability for organic photodiodes for vertically-integrated (VI) CMOS image sensors application According to the present disclosure, when one of the active materials is (almost) transparent, this offers the following possibilities for respective devices and so on:

- Tuning overall absorption spectrum via tuning absorption of the partner p (the donor) active material only

- Tuning of exciton diffusion efficiencies of the partner (absorbing) material only
- Tuning of charge generation efficiencies through LUMO only (or almost)
- Tuning of only electron mobility
- Generally: decoupling of absorption properties in the visible range from electron/hole transfer and transport properties

EXAMPLES

Example 1: Naphthalene Diimide (NDI)-Based Material

The naphthalene diimide (NDI) NDI1 has the following chemical structure:

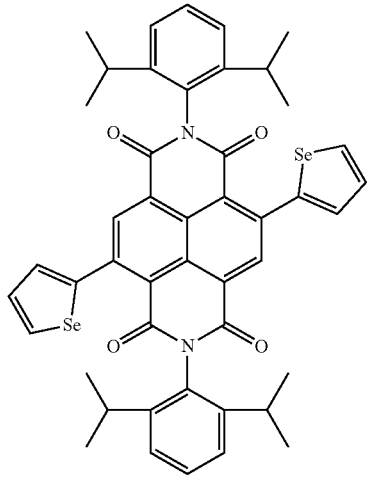

NDI 1
Chemical Formula: $C_{46}H_{42}N_2O_2Se_2$
Molecular Weight: 844.77

Figure 5:
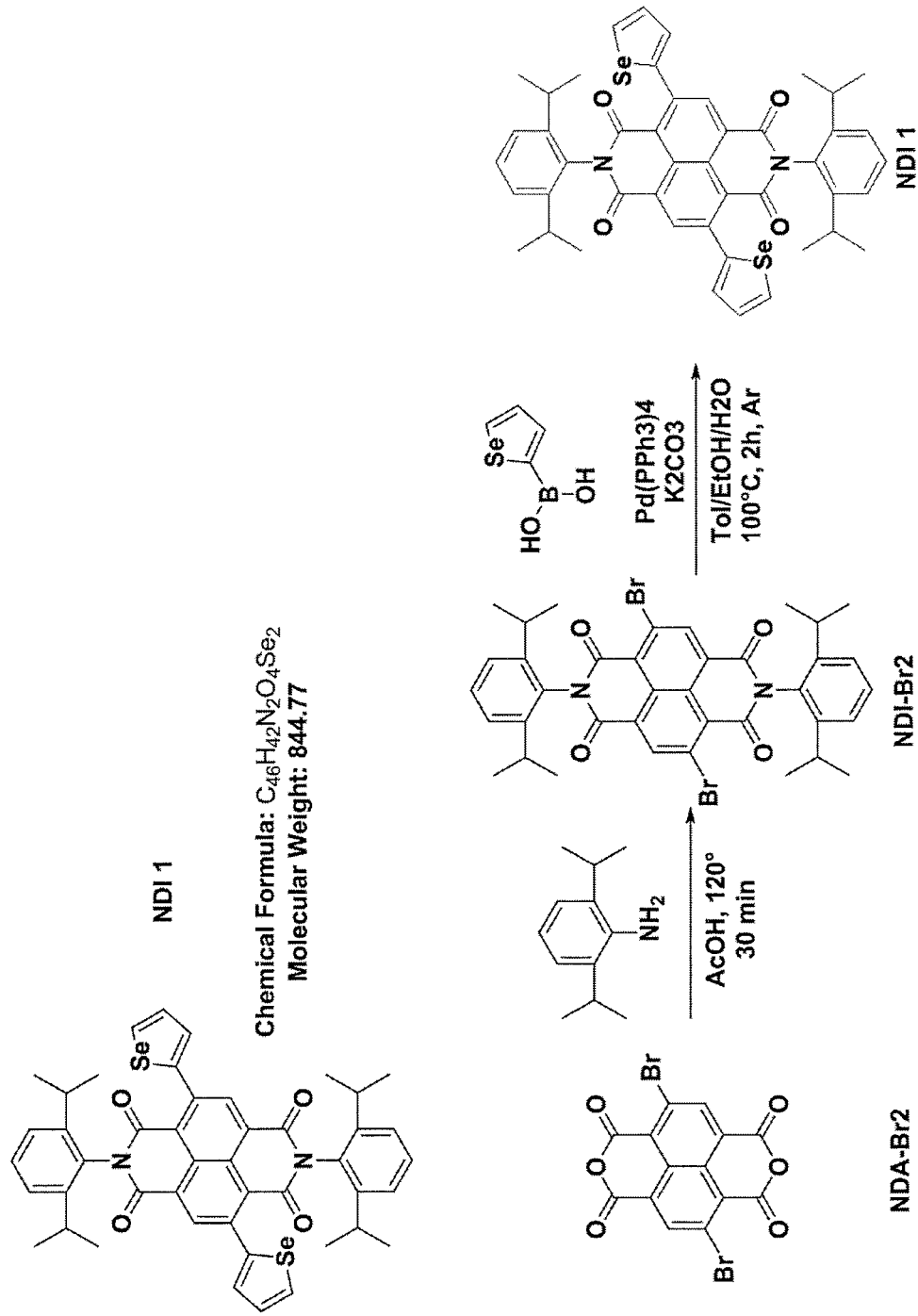
FIG. 5 shows naphthalene diimide (NDI) NDI1 and the general synthetic route for the material.
Figure 6:
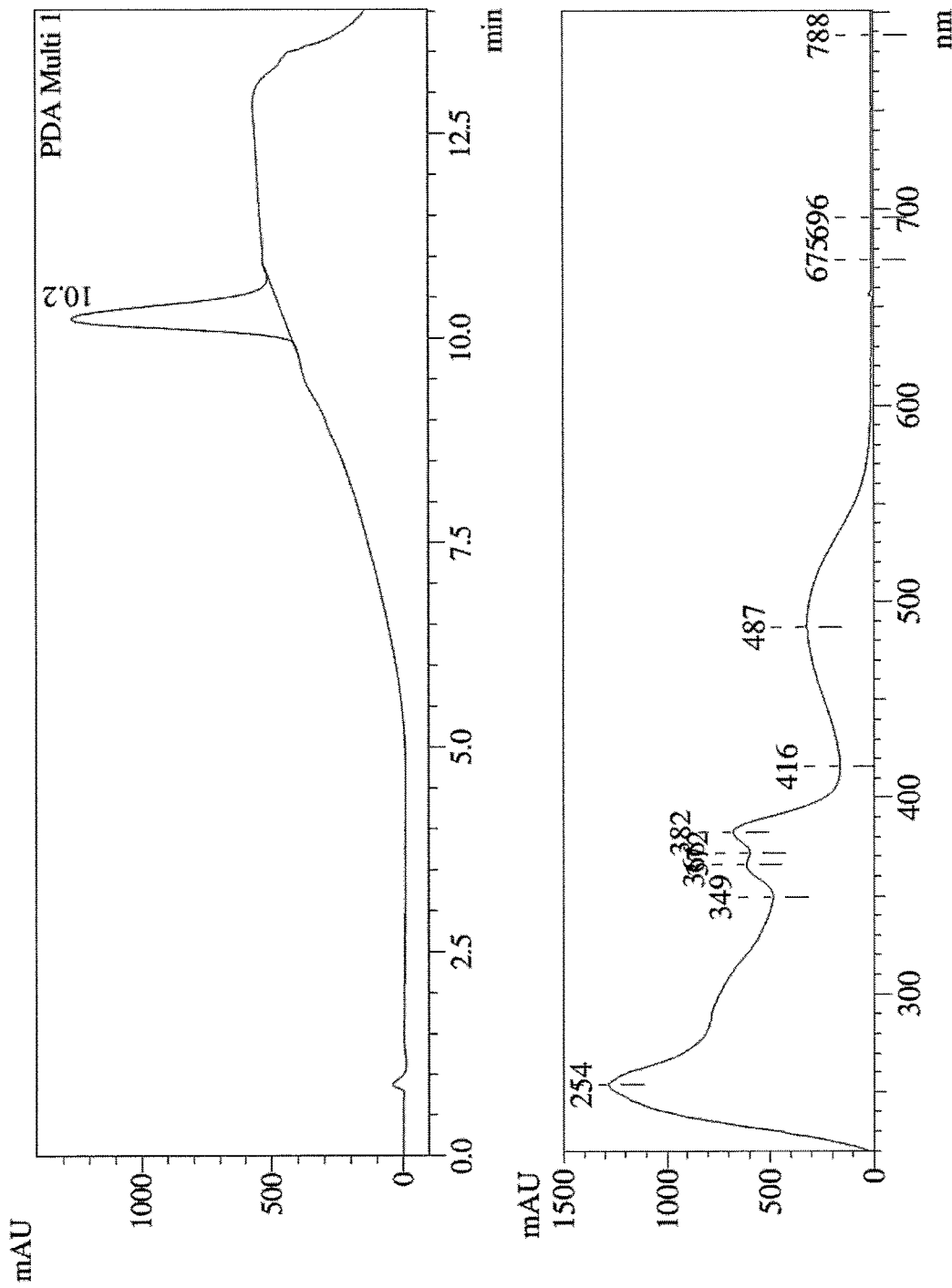
FIG. 6 shows HPLC analysis of NDI1.
Figure 7:
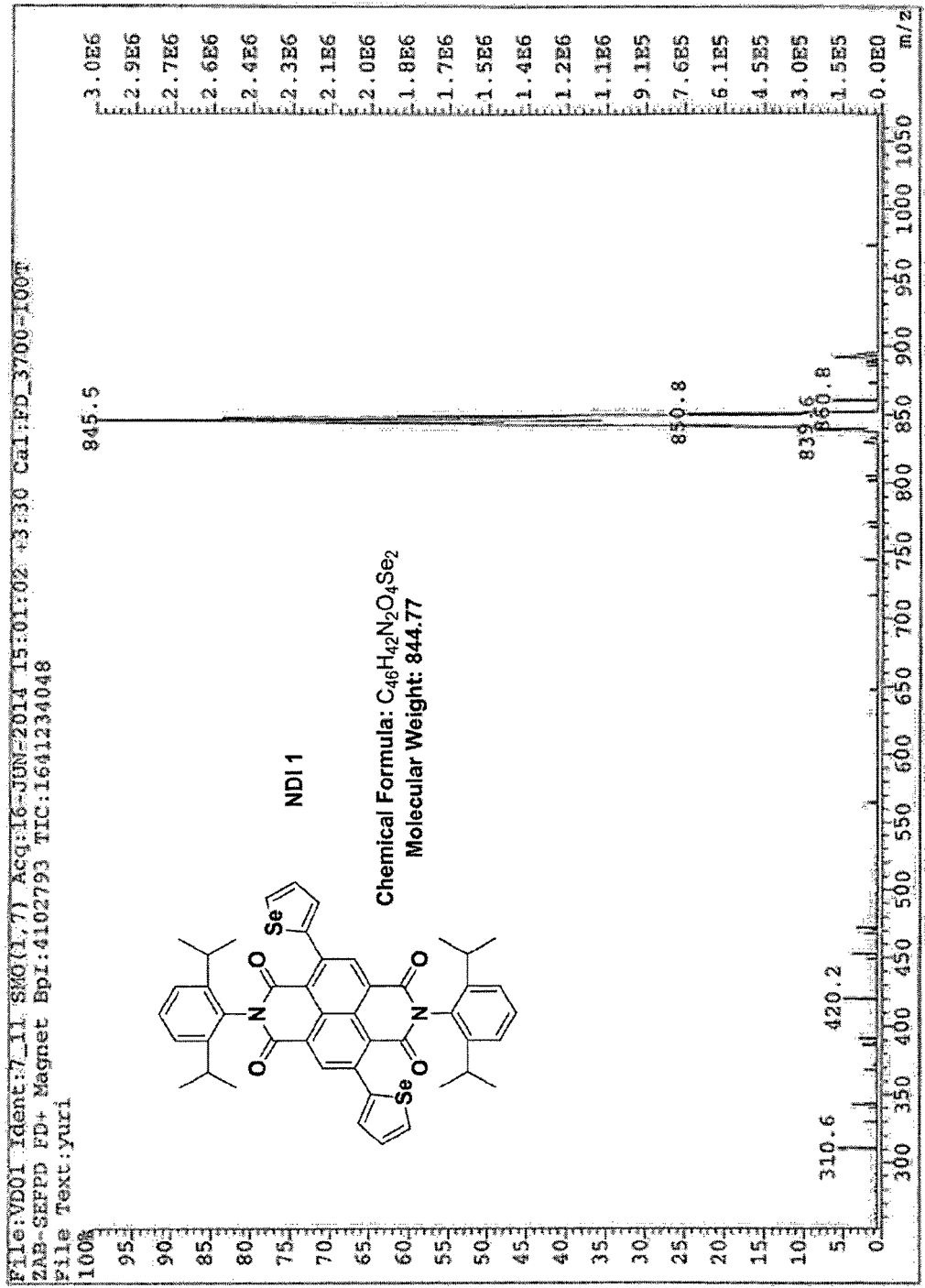
FIG. 7 shows FD mass analysis of NDI1.
Figure 8:
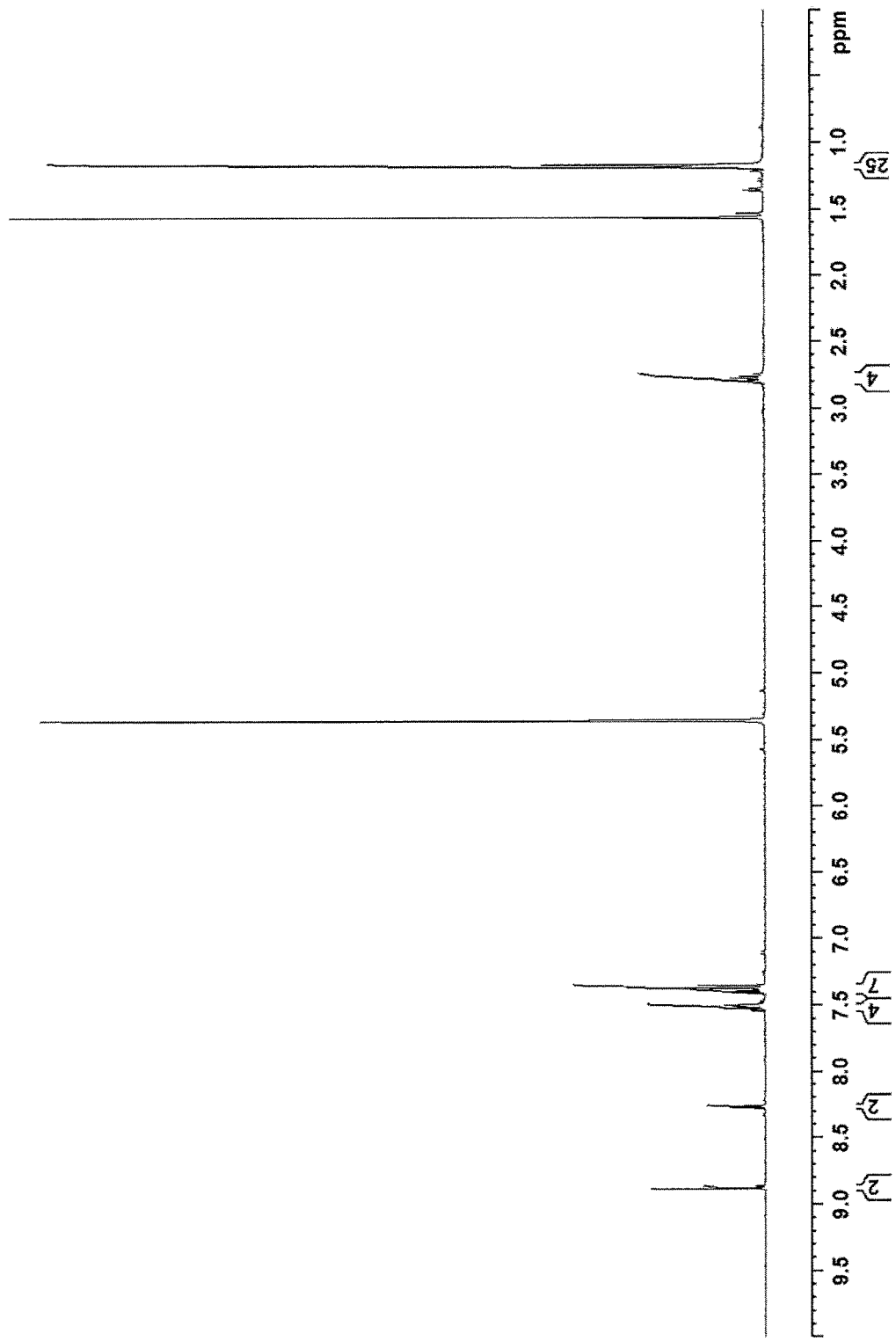
FIG. 8 shows $^1$H NMR analysis of NDI1.
Figure 9:
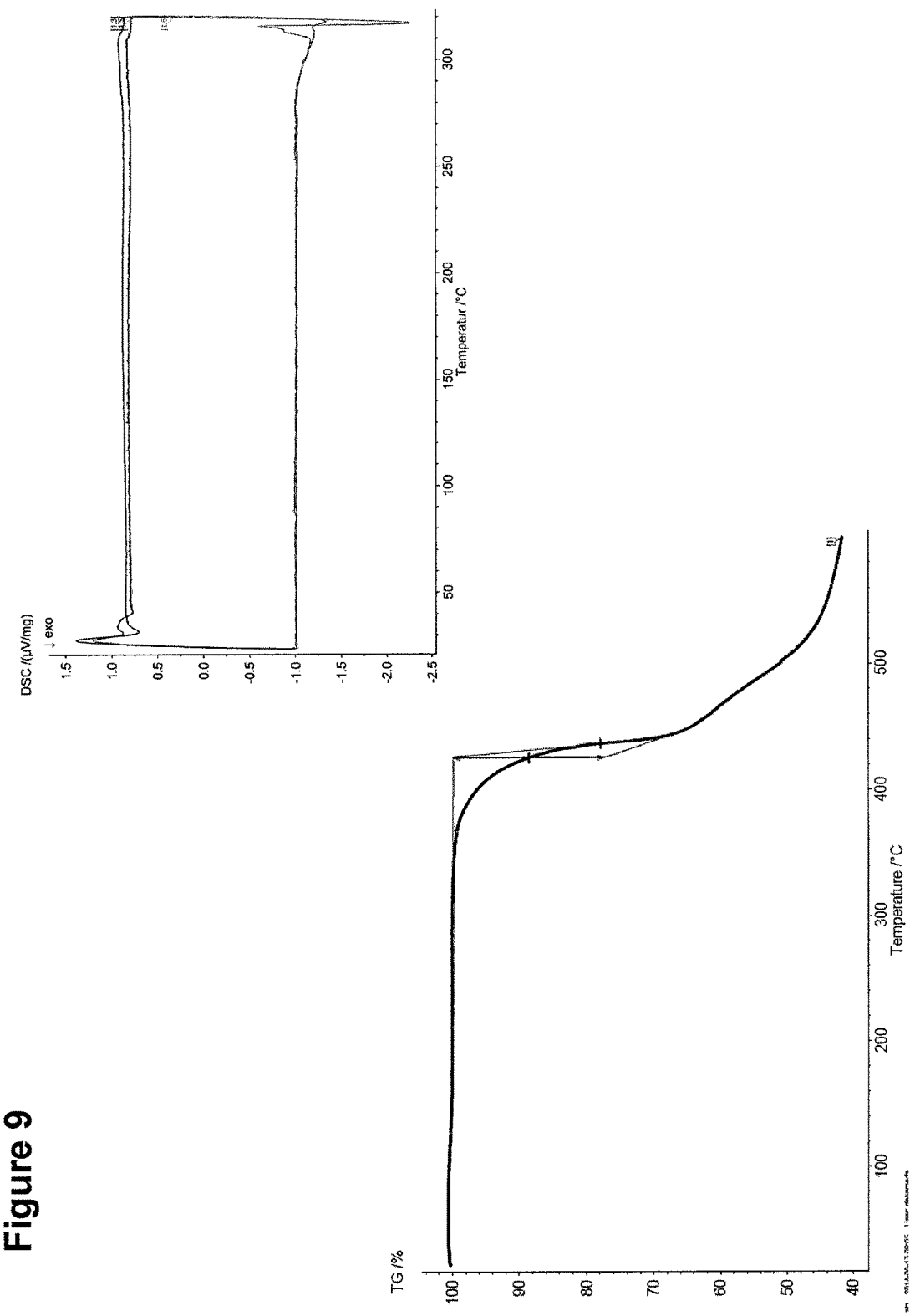
FIG. 9 shows TG and DSC analysis of NDI1.

In the scheme shown in FIG. 5, the general synthetic route for the synthesis of the material is reported.

The material NDI1 was characterised via HPLC, $^1$H NMR, Mass, TG and DSC. The data are shown in FIGS. 6 to 9.

Figure 10:
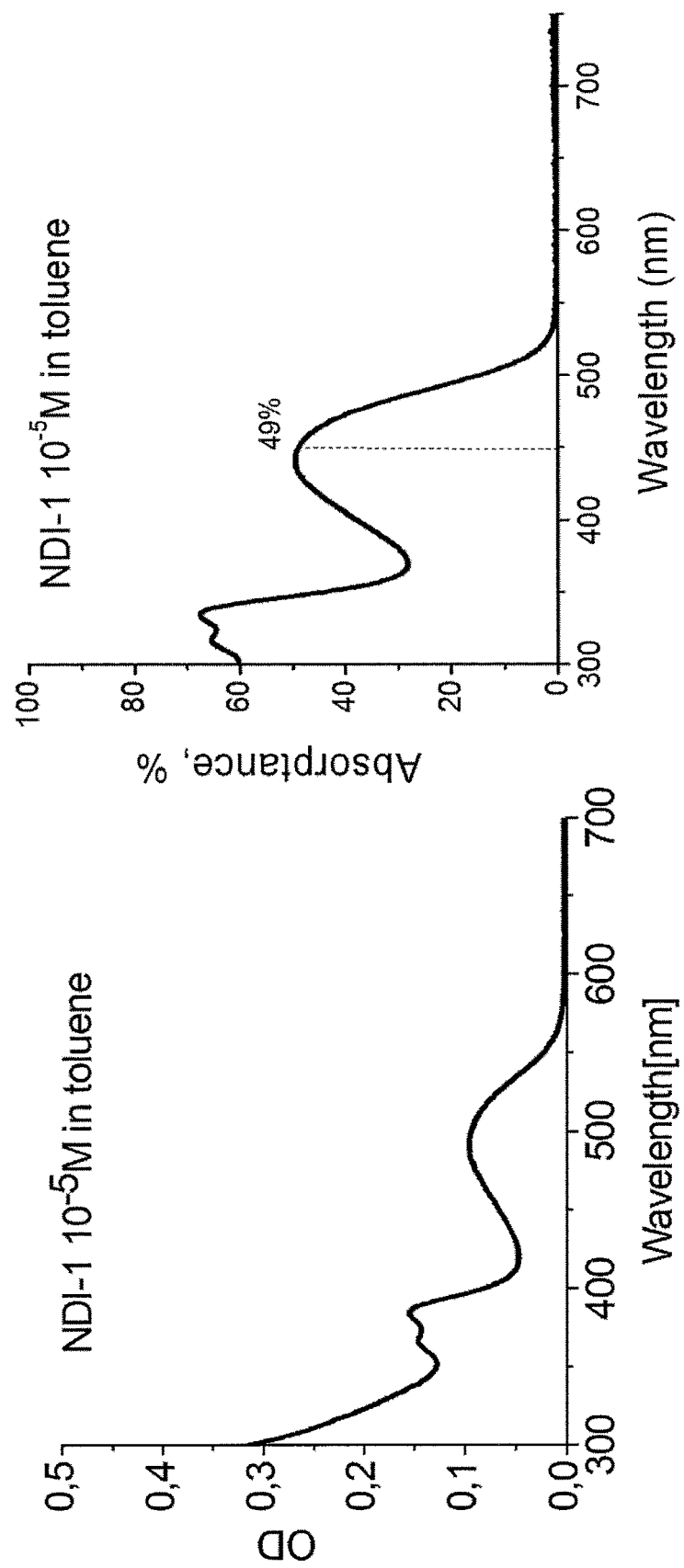
FIG. 10 shows UV VIS spectra of NDI1.
Figure 11:
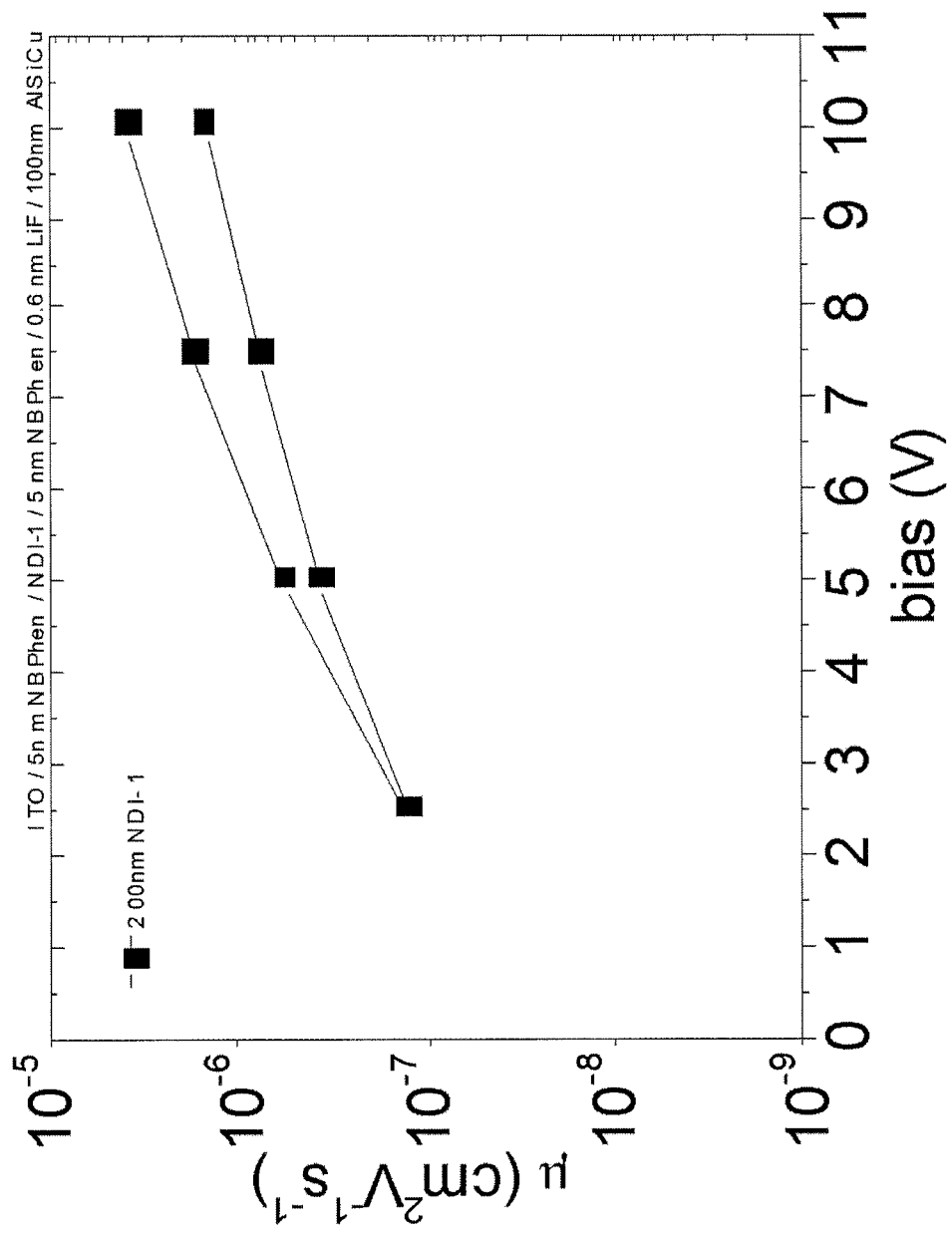
FIG. 11 shows electron mobilities of NDI1.

The absorption spectra showed a very low optical density in the visible range (FIG. 10). Electron mobilities are as high as $10^{-7}$ up to $10^{-5}$ cm$^2$/Vs (FIG. 11).

Figure 12:
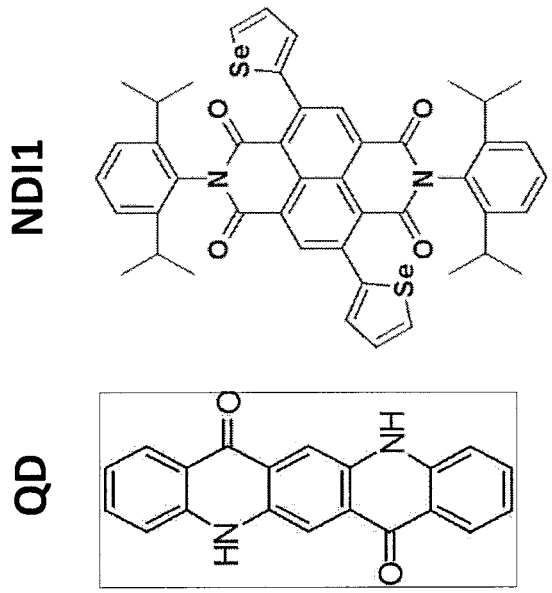
FIG. 12 shows a PiN junction device of NDI1 with QD.
Figure 12:
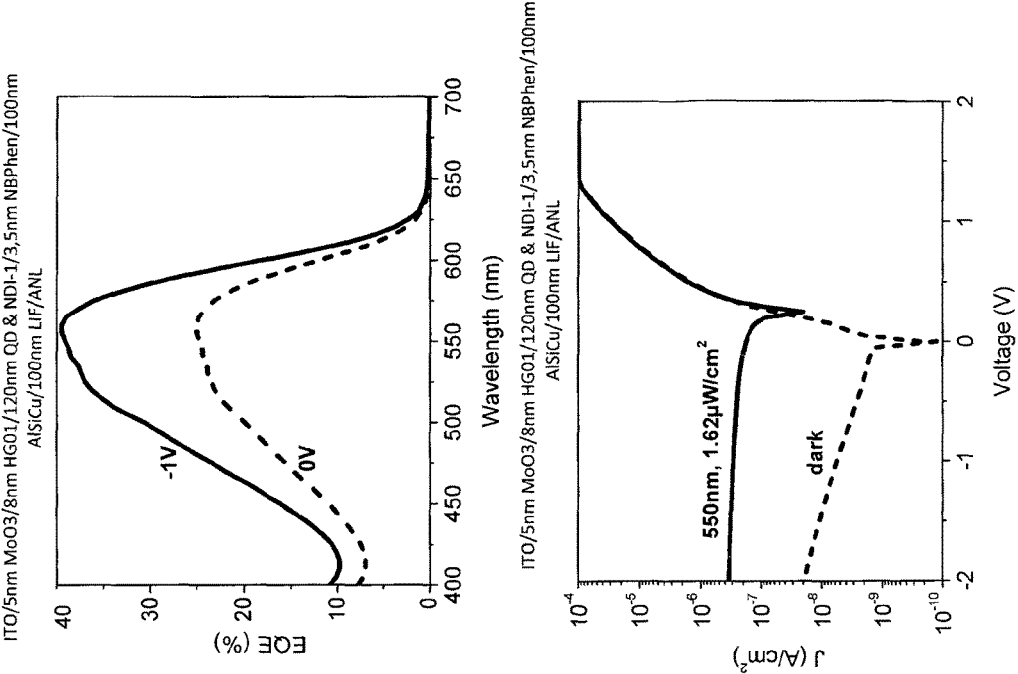
Figure 12:
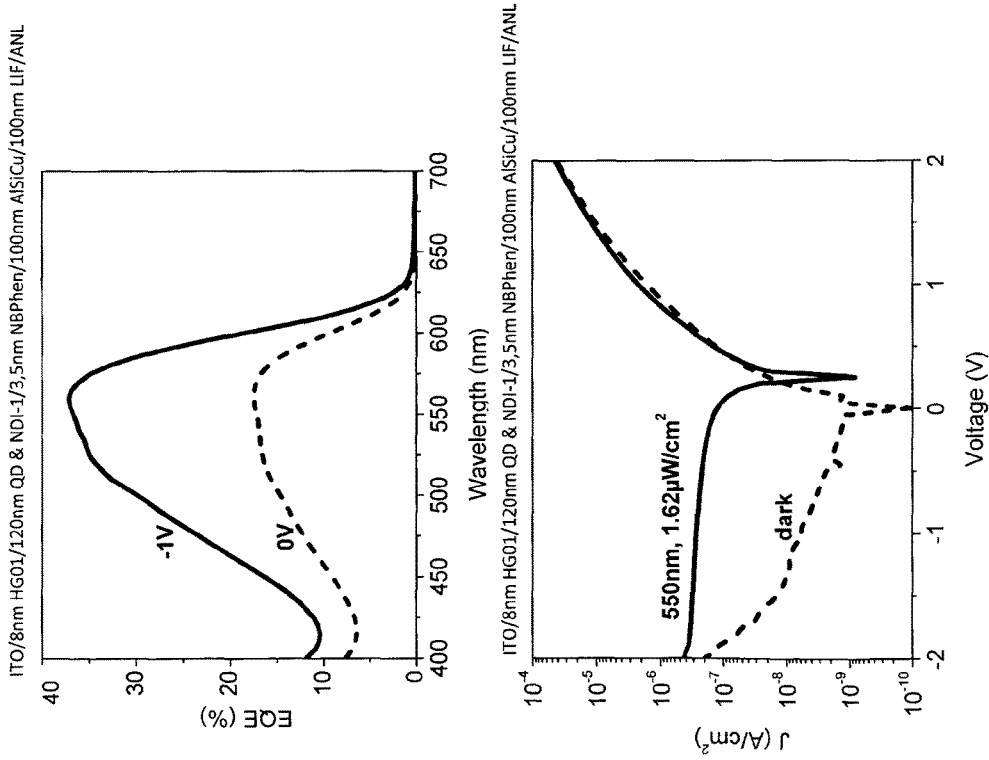
Figure 13:
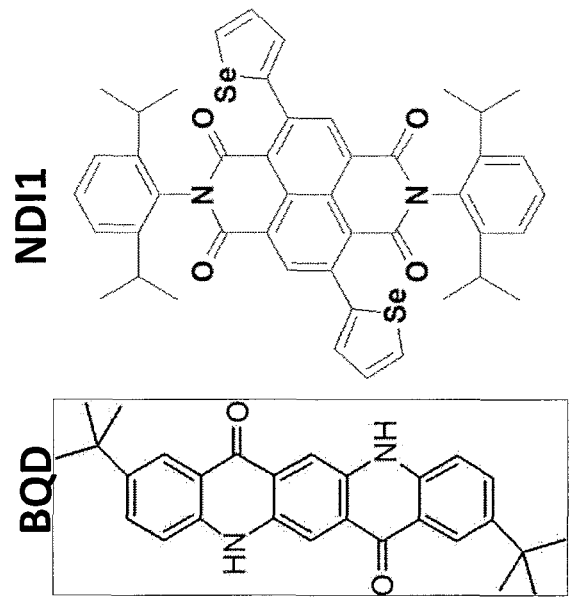
FIG. 13 shows a PiN junction device of NDI1 with BQD.
Figure 13:
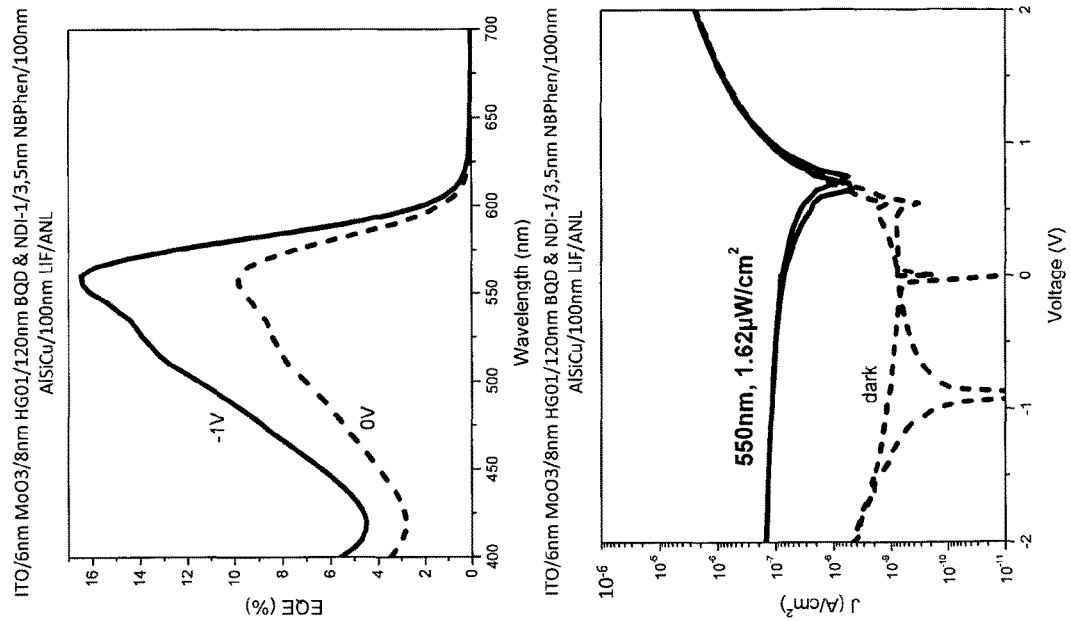
Figure 13:
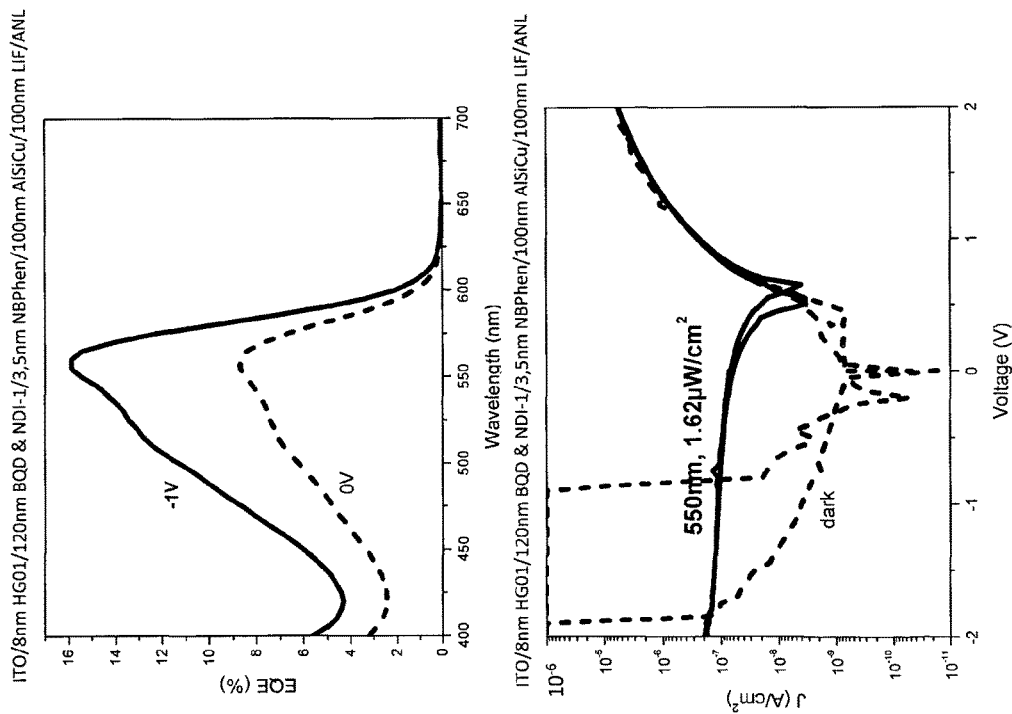

The NDI1 was used as acceptor material in combination with quinacridone (QD) and terButyl quinacridone (BQD) as donors in the following configurations:

ITO/8 nm HG01/120 nm QD & NDI1(1:1)/3,5 nmNBPhen/100 nm AlSiCu/100 nm LiF
ITO/5 nm MoO3/8 nm HG01/120 nm QD & NDI1(1:1)/3,5 nmNBPhen/100 nm AlSiCu/100 nm LiF
ITO/8 nm HG1/120 nm BQD & NDI1(7:3)/3,5 nmNBPhen/100 nm AlSiCu/100 nm LiF
ITO/5 nm MoO03/8 nm HG01/120 nm BQD &NDI1(7:3)/3,5 nmNBPhen/100 AlSiCu/100 nm LiF The devices were characterised by measuring IV dark, IV light (1.62 µW/cm2, 550 nm) and action spectra @ 0V and −1V. The results are shown in FIGS. 12 and 13.

Figure 14:
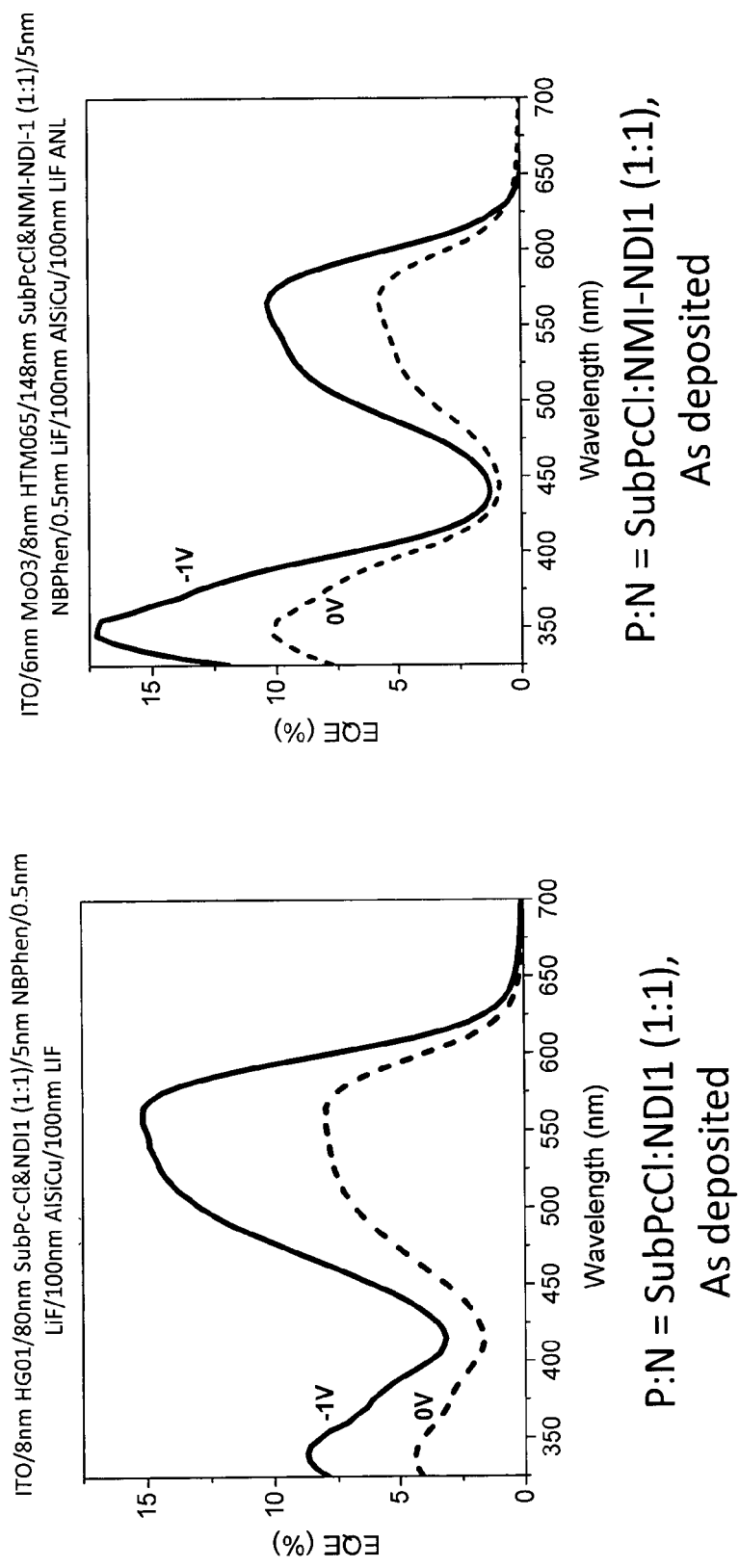
FIG. 14 shows a PiN junction device of NDI1 with SubPcCl and of NMI-NDI1 with SubPcCl.

The NDI1 or NMI-NDI1 were used as acceptor materials in combination with Subphtalocyaninechloride (SubPcCl) as donor in the following configurations:

ITO/8 nm HG01/80 nm SubPcCl & NDI1(1:1)/5 nmNBPhen/0.5 nm LiF/100 nm AlSiCu/100 nm LiF
ITO/6 nm MoO3/8 nm HTM065/148 nm SubPcCl & NMI-NDI1(1:1)/5 nm NBPhen/0.5 nm LiF/100 nm AiSiCu/100 nm LiF The devices were characterised by measuring action spectra @ 0V and −1V. The results are shown in FIG. 14.

Example 2: Further naphthalene diimide (NDI)-based materials

The naphthalene diimides (NDI) NDI20-26, NDI 28-29 and NDI35-38 have the following chemical structures:

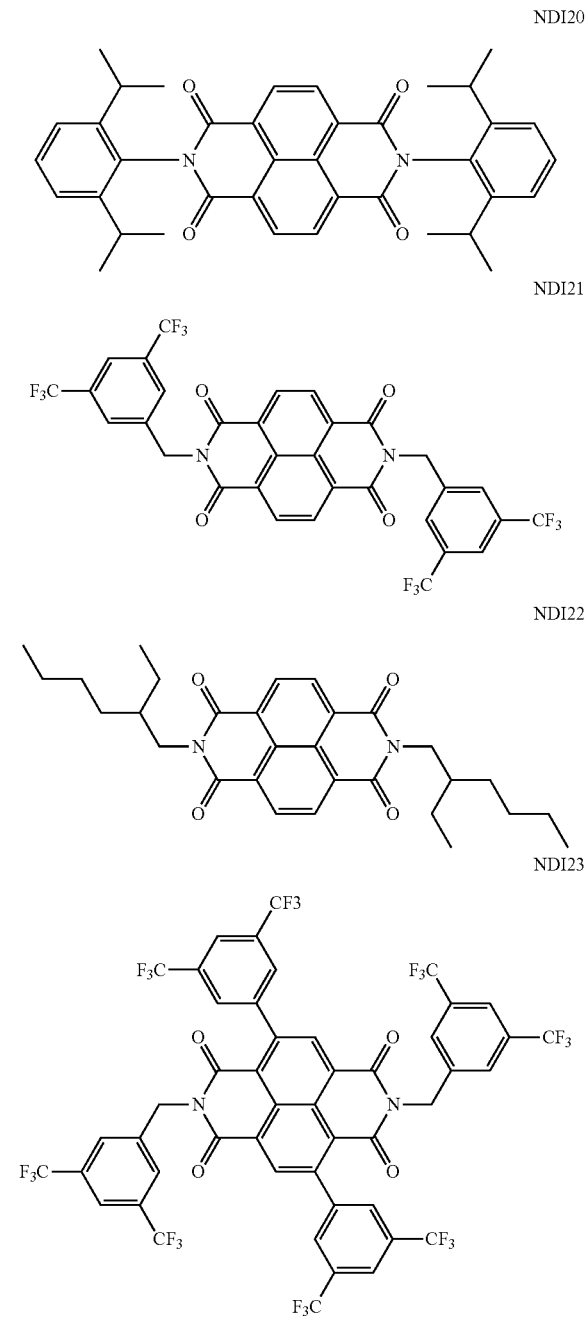

NDI24
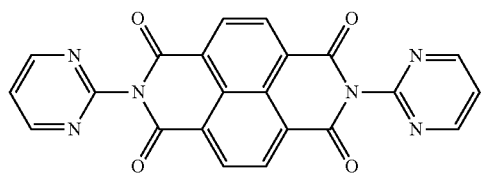

NDI26
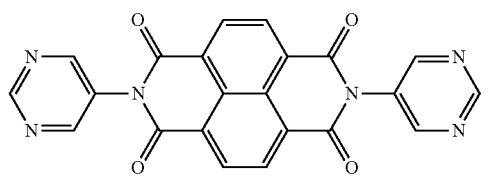

NDI28
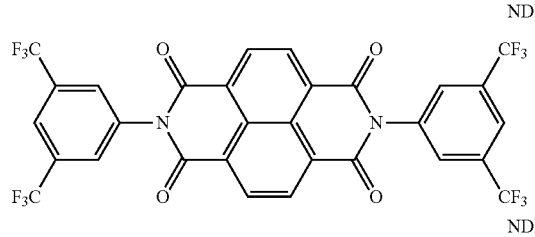

NDI29
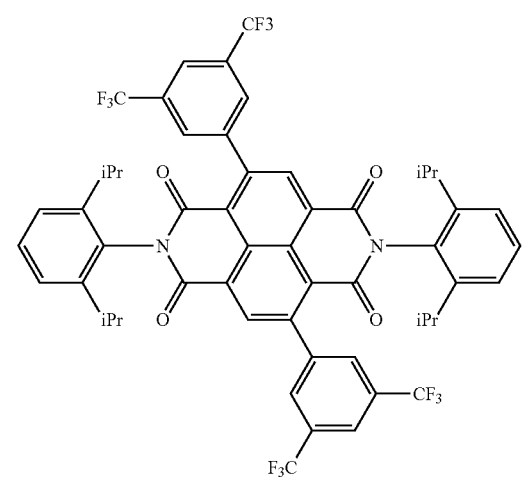

NDI35

NDI36

NDI37
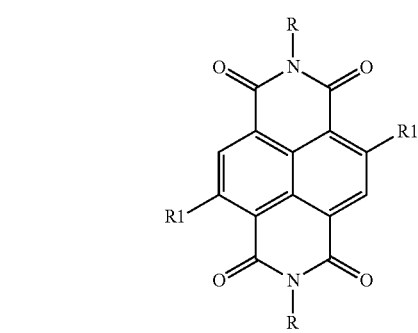

NDI38

Figure 15:
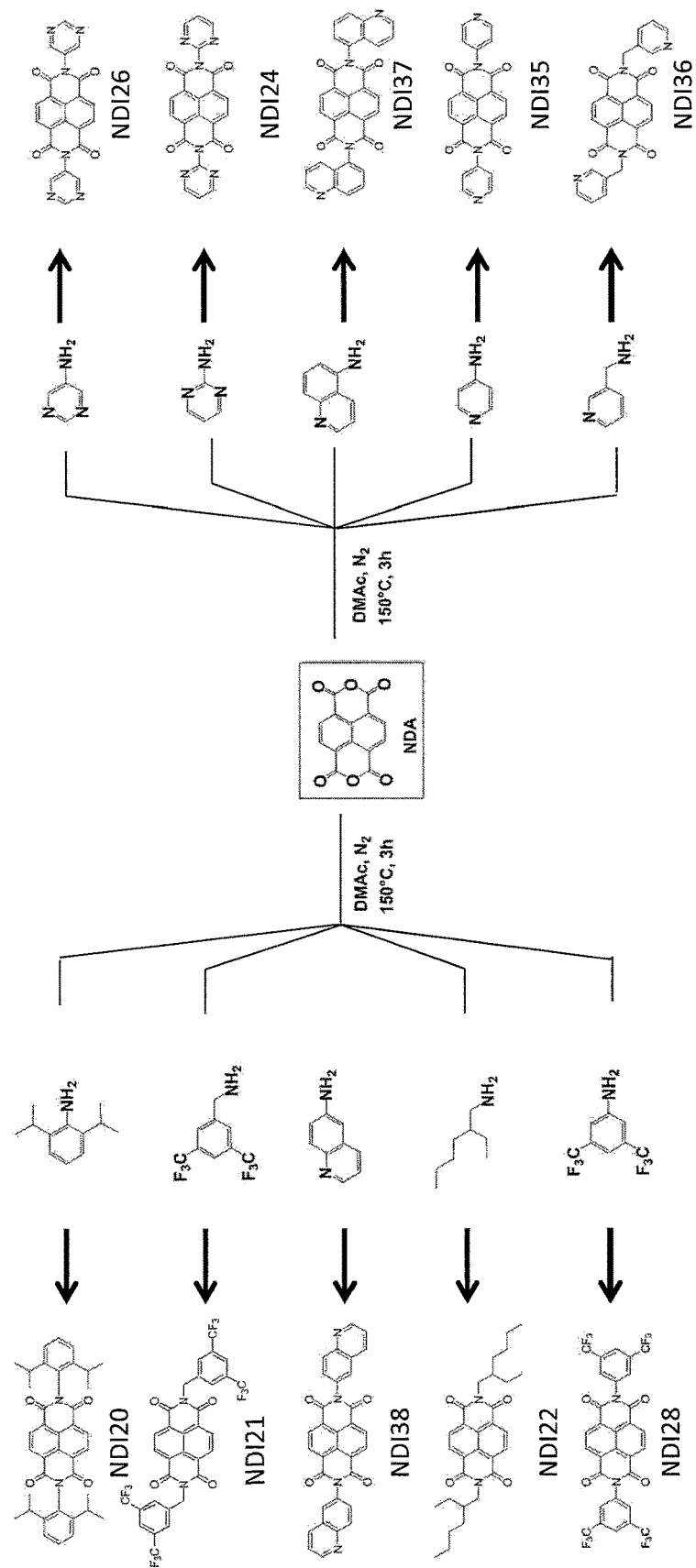
FIG. 15 show s a synthesis overview for NDI materials with general formula Ia.

In the scheme shown in FIG. 15, the general synthetic route for the synthesis of the materials is reported.

The NDI materials showed absorption maxima in the range of 379 to 385 nm (FIG. 16).

Figure 17:
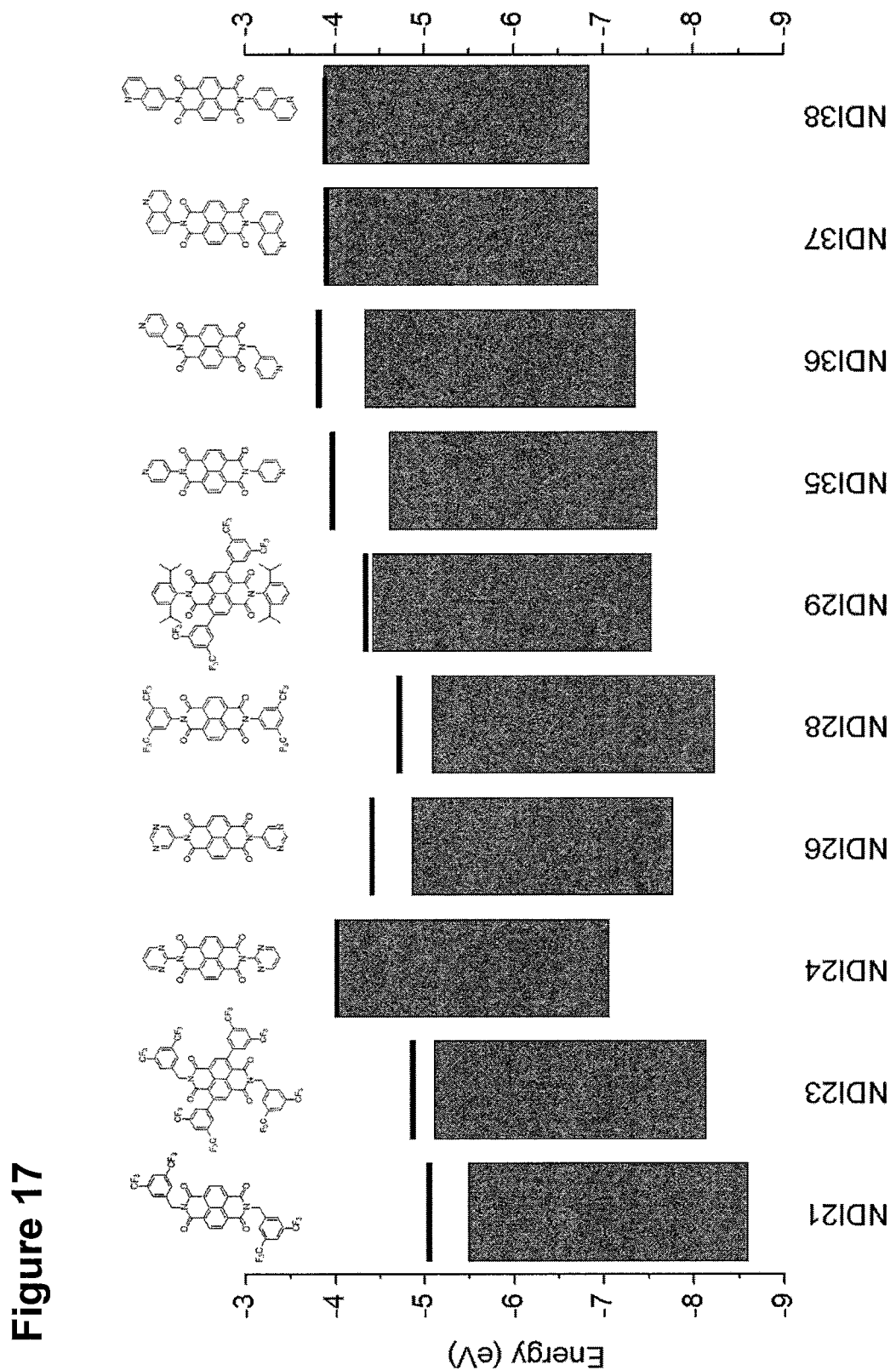
FIG. 17 shows energy levels of N-buffer materials with general formula Ia.
Figure 18:
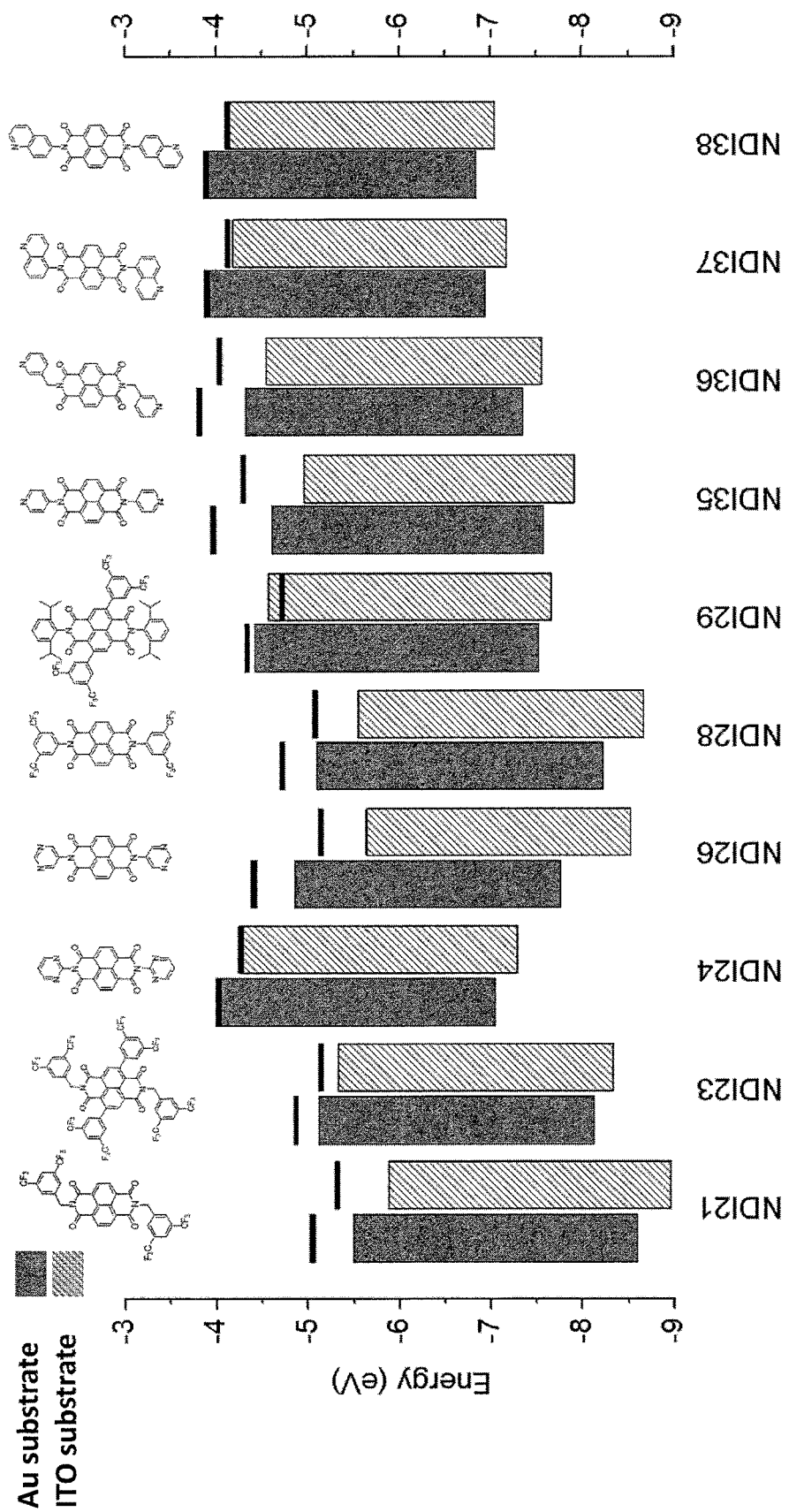
FIG. 18 shows energy levels of N-buffer materials with general formula Ia.

Energy levels are shown in FIGS. 17 to 19.

NDI35 was used as n-buffer material in devices of DTT2, DTT9, DIT10 or DTT11, respectively, with F6SubPcOC6F5 in the following configurations: LiF 150 nm/AlSiCu 100 nm/NDI35 10 nm/DTT9: F6SubPcOC6F5 (1:1) 200 nm/ST1163 10 nm/ITO/glass.

Figure 20:
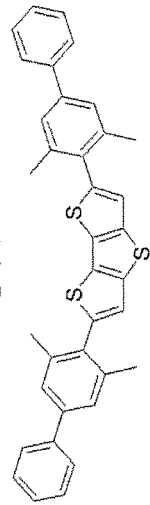
FIG. 20 and 21 show devices of NDI35 as n-buffer with different p materials.
Figure 20:
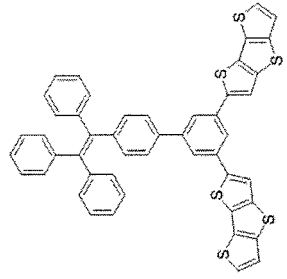
Figure 20:
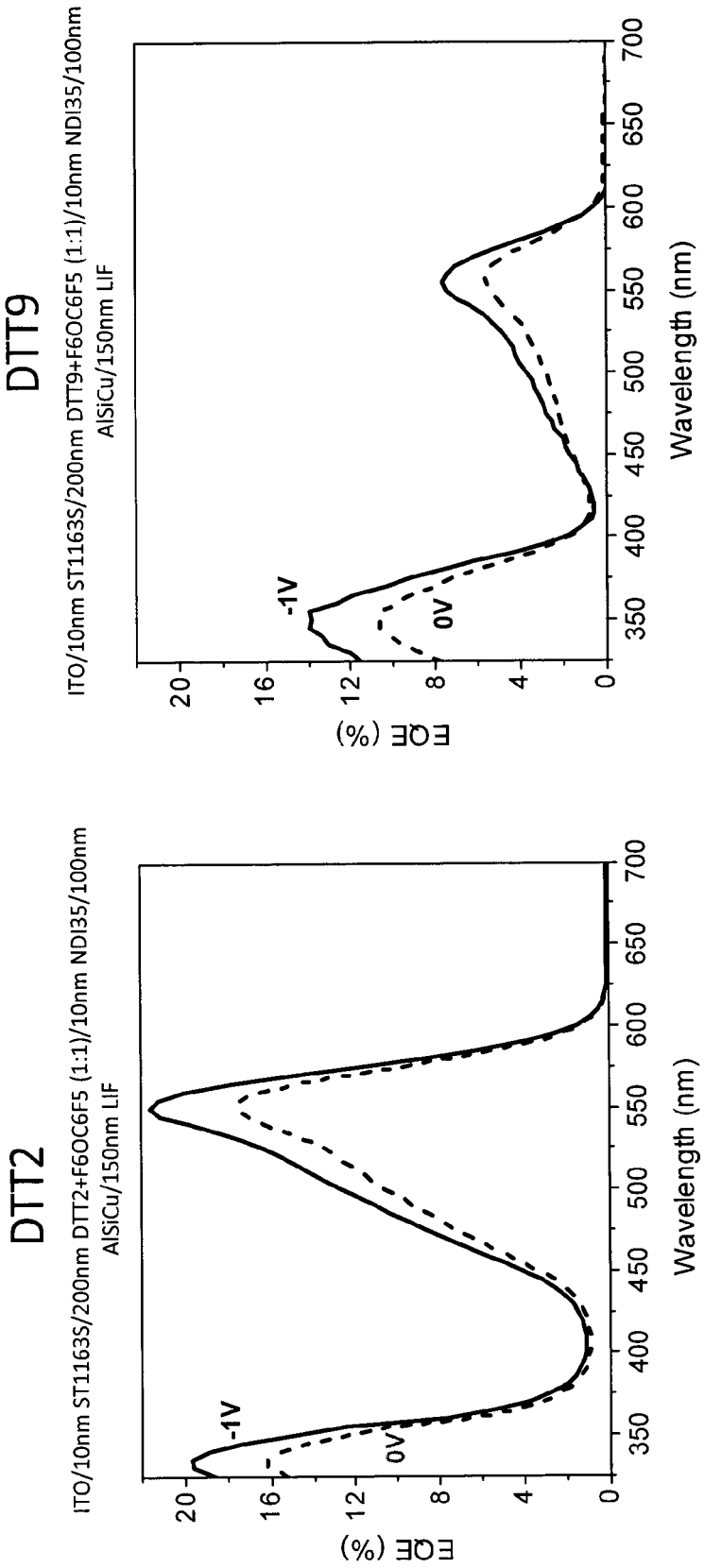
Figure 20:
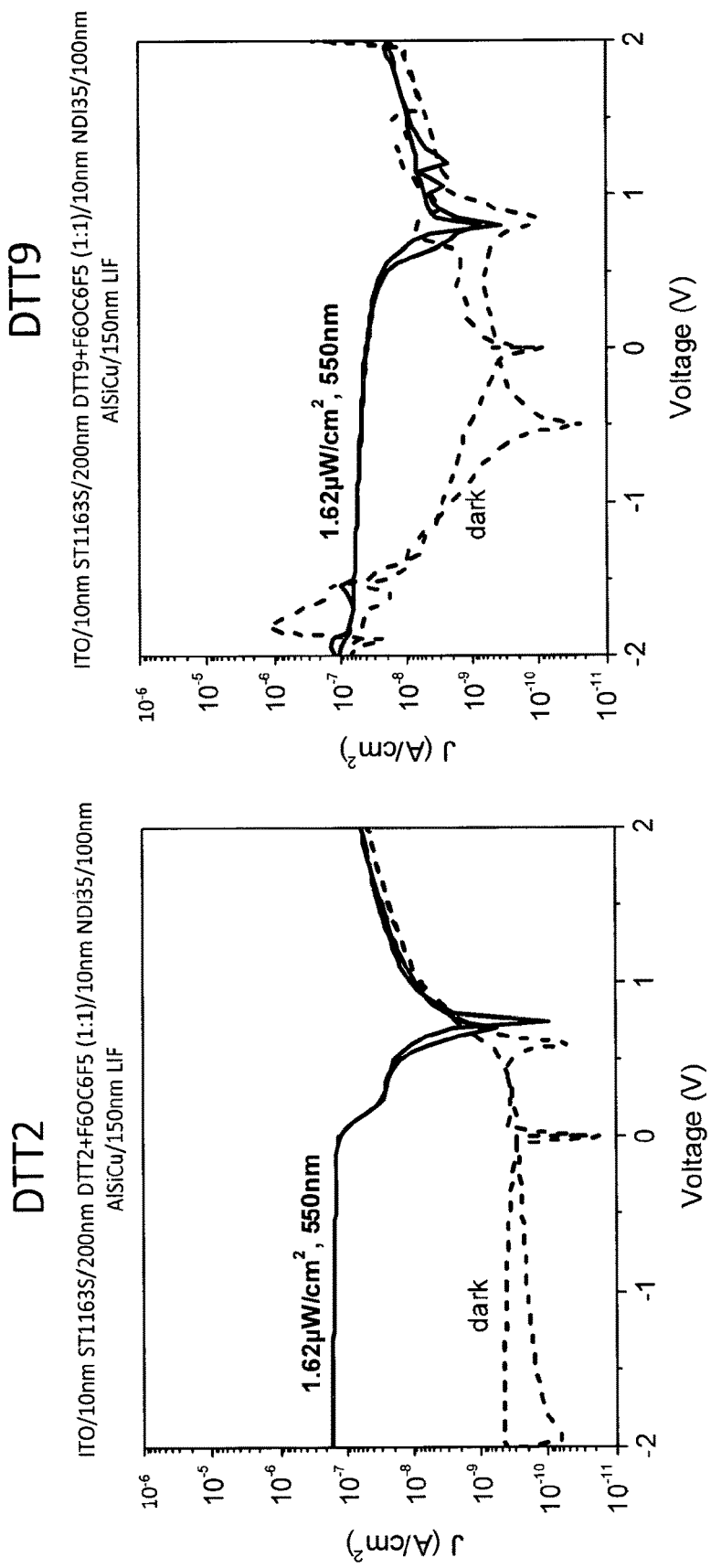
Figure 21:
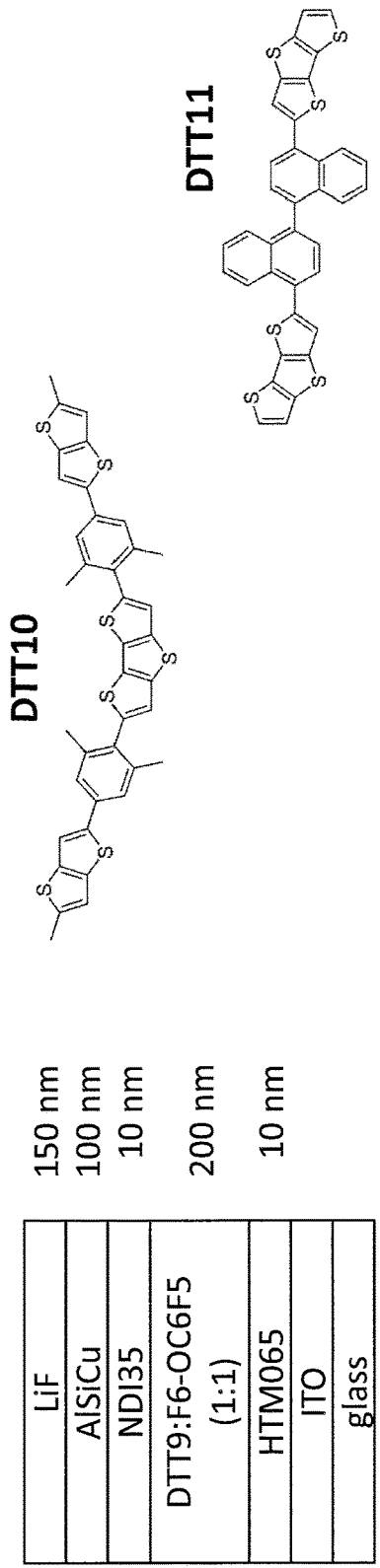
Figure 21:
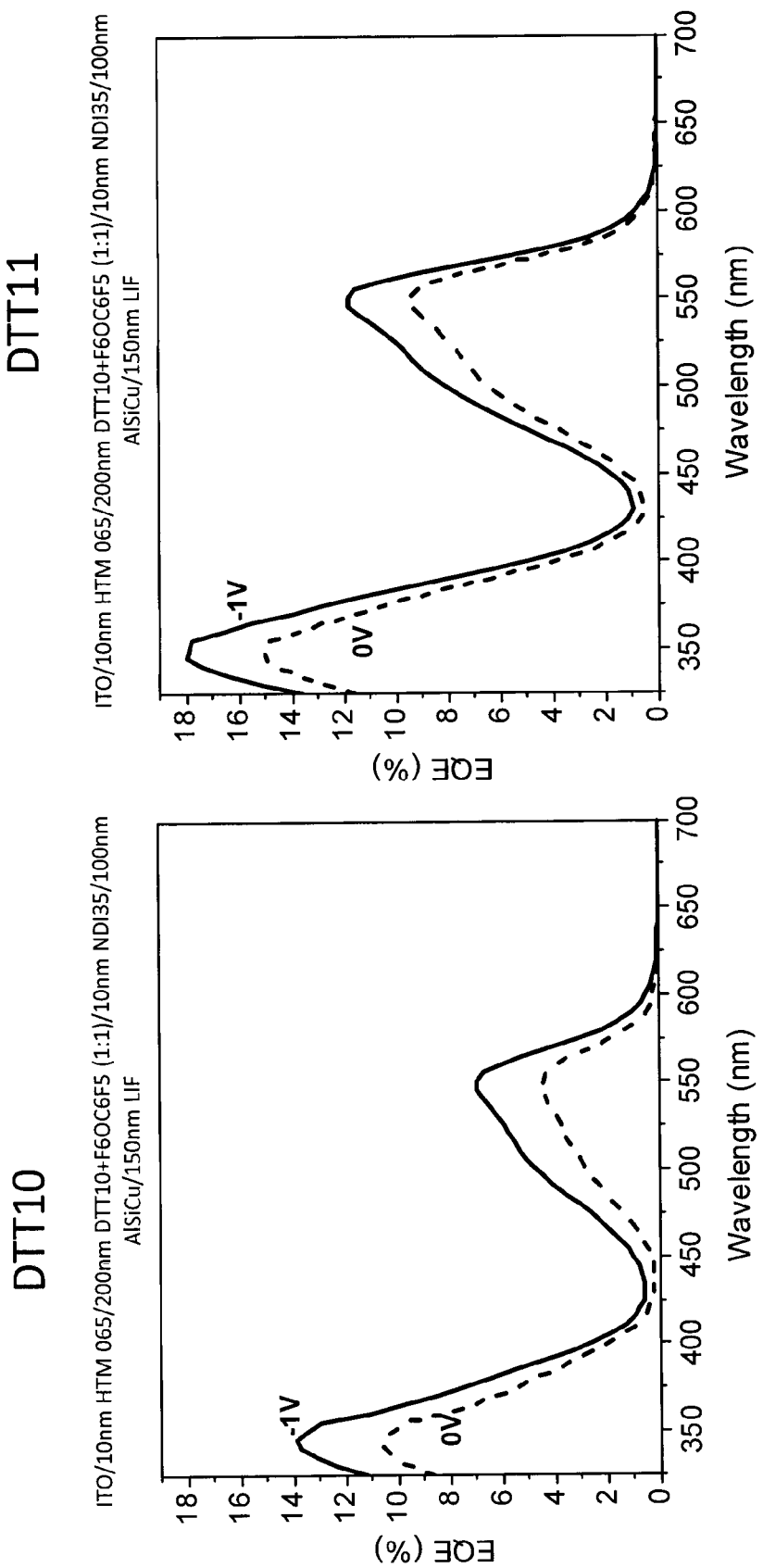
Figure 21:
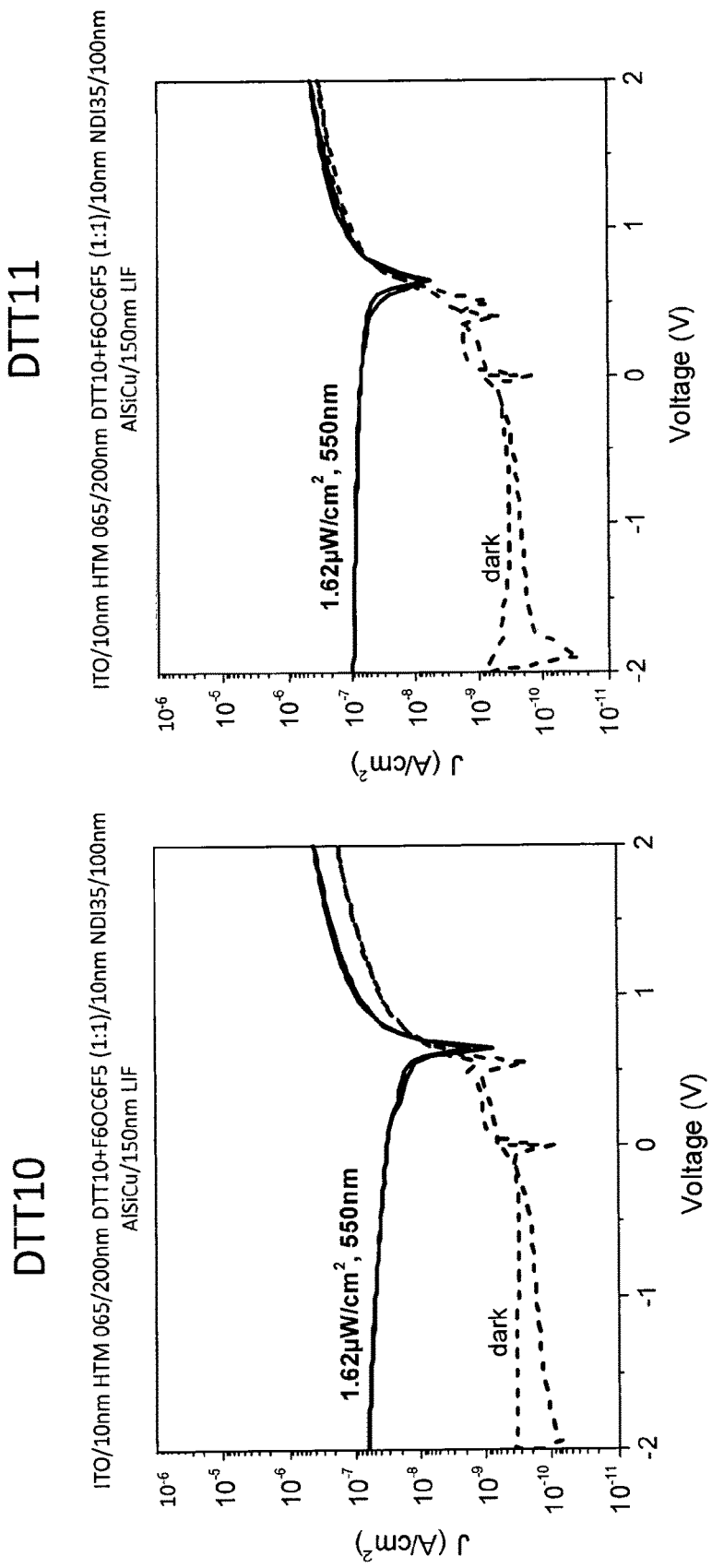

The devices were characterized, e.g. by measuring action spectra @ 0V and −1V. The results are shown in FIGS. 20 and 21.

The present application claims priority to European Patent Application 15162042.4 filed by the European Patent Office on 31 Mar. 2015, the entire contents of which being incorporated herein by reference.

The invention claimed is:
1. A naphthalene diimide (NDI)-based molecule represented by formula I

I wherein
each R is

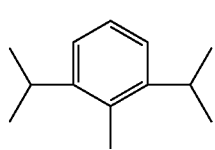

and
each $R_1$ is

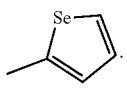

2. A transparent N or P or ambipolar material, comprising the naphthalene diimide (NDI)-based molecule of claim 1.

3. The transparent N or P or ambipolar material of claim 2, which
has an absorption coefficient of less than about 60,000 cm$^{-1}$ in visible wavelength range, and
is an organic based compound forming homogenous films using vacuum deposition or spin coating.

4. A P:N heterojunction or a bi(multi) layer junction, comprising
the naphthalene diimide (NDI)-based molecule of claim 1, and
optionally a further N and/or P material,
wherein the further N and/or P material exhibits absorption in visible wavelength range.

5. A method for making an absorption layer, the method comprising:
introducing the naphthalene diimide (NDI)-based molecule of claim 1, and
optionally a further N and/or P material into the absorption layer,
wherein the further N and/or P material exhibits absorption in visible wavelength range.

6. A method for making a photoelectric conversion layer and/or an organic and/or hybrid module for optoelectronic application, the method comprising:
introducing the naphthalene diimide (NDI)-based molecule of claim 1, and optionally a further N and/or P material
into the photoelectric conversion layer and/or the organic and/or hybrid module for optoelectronic application,
wherein the further N and/or P material exhibits absorption in visible wavelength range.

7. A photoelectric conversion layer, comprising the naphthalene diimide (NDI)-based molecule of claim 1,
optionally a further N and/or P material, wherein the further N and/or P material exhibits absorption in visible wavelength range
and optionally at least one further molecule.

8. An absorption layer, comprising the naphthalene diimide (NDI)-based molecule of claim 1,
optionally a further N and/or P material, and
optionally at least one molecule,
wherein the further N and/or P material exhibits absorption in visible wavelength range.

9. A device, comprising at least one naphthalene diimide (NDI)-based molecule of claim 1,
wherein said device is an organic image sensor, an hybrid image sensor, photodiode, an organic photovoltaic, an organic light-emitting diode (OLED), or an organic thin-film transistor (OTFT).

10. The device according claim 9, further comprising at least one further N and/or P material exhibiting absorption in visible wavelength range,
and/or at least one further molecule.

11. An organic image sensor, comprising
(a) an organic photoelectric conversion unit comprising at least one photoelectric conversion layer of claim 7,
(b) at least one electrode,
(c) a substrate, and
(d) optionally, a second electrode on top of the at least one photoelectric conversion layer.

12. A hybrid Silicon-organic image sensor or an organic image sensor, comprising
(a) an organic photoelectric conversion unit or units comprising at least one photoelectric conversion layer of claim 7,
(b) optionally, a Si based photoelectric conversion unit,
(c) metal wiring,
(d) a (CMOS) substrate, and
(e) at least one insulating layer.

13. The organic image sensor according to claim 11, wherein said organic photoelectric conversion unit comprises different layers.

14. A method for synthesizing transparent n materials, comprising
imidizing 2,6-dibromonaphthalene-1,4,5,8-tetracarboxylic dianhydride derivatives in the presence of a R-primary amine and acid, and
subsequently performing a palladium catalyzed Suzuki Coupling with a R1-boronic ester, to obtain the naphthalene diimide (NDI)-based molecule of claim 1.

\* \* \* \* \*